US010202609B2

(12) United States Patent
Lee et al.

(10) Patent No.: US 10,202,609 B2
(45) Date of Patent: Feb. 12, 2019

(54) MICROORGANISMS PRODUCING L-AMINO ACIDS AND PROCESS FOR PRODUCING L-AMINO ACIDS USING THE SAME

(71) Applicant: CJ CHEILJEDANG CORP., Seoul (KR)

(72) Inventors: Ji Sun Lee, Incheon (KR); Chang Il Seo, Incheon (KR); Ki Yong Cheong, Gimpo-si (KR); Eun Sung Koh, Suwon-si (KR); Do Hyun Kwon, Seoul (KR); Kwang Ho Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/112,826

(22) PCT Filed: Mar. 17, 2015

(86) PCT No.: PCT/KR2015/002548
§ 371 (c)(1),
(2) Date: Jul. 20, 2016

(87) PCT Pub. No.: WO2015/142020
PCT Pub. Date: Sep. 24, 2015

(65) Prior Publication Data

US 2017/0044553 A1 Feb. 16, 2017

(30) Foreign Application Priority Data

Mar. 21, 2014 (KR) ........................ 10-2014-0033697

(51) Int. Cl.

| | |
|---|---|
| ***C12N 1/20*** | (2006.01) |
| ***C12P 13/08*** | (2006.01) |
| ***C12P 13/22*** | (2006.01) |
| ***C12N 15/70*** | (2006.01) |
| ***C07K 14/245*** | (2006.01) |

(52) U.S. Cl.
CPC ............ *C12N 15/70* (2013.01); *C07K 14/245* (2013.01); *C12N 1/20* (2013.01); *C12P 13/08* (2013.01); *C12P 13/227* (2013.01)

(58) Field of Classification Search
None
See application file for complete search history.

(56) References Cited

U.S. PATENT DOCUMENTS

| | | | |
|---|---|---|---|
| 8,932,834 B2 | 1/2015 | Doi et al. | |
| 2008/0009041 A1 | 1/2008 | Mizoguchi et al. | |
| 2011/0111458 A1* | 5/2011 | Masuda ............... | C07K 14/245 435/69.1 |

FOREIGN PATENT DOCUMENTS

| | | | |
|---|---|---|---|
| JP | 2012223092 | A | 11/2012 |
| KR | 1020070086634 | A | 8/2007 |
| WO | 2004087895 | A1 | 10/2004 |
| WO | 2006057341 | A1 | 6/2006 |
| WO | 2006063362 | A1 | 6/2006 |
| WO | 2007119891 | A1 | 10/2007 |
| WO | 2008146682 | A1 | 12/2008 |
| WO | 2012099396 | A2 | 7/2012 |

OTHER PUBLICATIONS

Hildegard Etz et al., Bacterial Phage Receptors, Versatile Tools for Display of Polypeptides on the Cell Surface, Journal of Bacteriology, vol. 183 (23), pp. 6924-6935 (Dec. 2001).
International Search Report for International Application No. PCT/KR2015/002548 dated Jun. 19, 2015.
McPartland et al., The Tail Sheath of Bacteriophage N4 Interacts with the *Escherichia coli* Receptor, Journal of Bacteriology, vol. 191 (2), pp. 525-532 (Jan. 2009).
Written Opinion for International Application No. PCT/KR2015/002548 dated Jun. 19, 2015.
Diane R. Kiino et al., Genetic Analysis of Bacteriophage N4 Adsorption, 1989, pp. 4595-4602, Journal of Bacteriology.
Haiyan Zhou et al., Enhanced L-phenylalanine production by recombinant *Escherichia coli* BR-42 (pAP-B03) resistant to bateriophage BP-1 via a two-stage feeding approach, 2011, pp. 1219-1227.
Tomoya Baba et al., Construction of *Escherichia coli* K-12 in-frame, single-gene knockout mutants: the Keio collection, 2006, 59 pages, Molecular Systems Biology.
Paul A. Manning et al., Outer Membrane of *Escherichia coli* K-12: TSX Mutants (Resistant to Bacteriophage T6 and Colicin K) Lack an Outer Membrane Protein, 1976, pp. 466-471, vol. 71, No. 2, Biochemical and Biophysical Research Communications.
Extended Eropean Search Report dated Oct. 18, 2017 of the European Patent Application No. 15765883.2.
English Translation of Japanese Office Action for Application No. 2016-567319 dated Jul. 25, 2017 (previously cited in IDS filed on Sep. 21, 2017).

* cited by examiner

*Primary Examiner* — Richard C Ekstrom
(74) *Attorney, Agent, or Firm* — Cantor Colburn LLP

(57) ABSTRACT

Disclosed are a recombinant microorganism having enhanced L-amino acid producibility, wherein the recombinant microorganism is transformed to have an inactivated phage receptor thereof, and a method of producing an L-amino acid using the recombinant microorganism. The use of the recombinant microorganism may enable the production of the L-amino acid in a highly efficient manner.

13 Claims, No Drawings

Specification includes a Sequence Listing.

SEQUENCE LISTING

<160> NUMBER OF SEQ ID NOS: 51

<210> SEQ ID NO 1
<211> LENGTH: 70
<212> TYPE: DNA
<213> ORGANISM: Artificial Sequence
<220> FEATURE:
<223> OTHER INFORMATION: primer for inactivating nfrA

<400> SEQUENCE: 1
atgaaggaga ataaccttaa tcgcgtcatc ggatggtctg gtttactgct gacgtcttta 60
ttgagtacca 70

<210> SEQ ID NO 2
<211> LENGTH: 71
<212> TYPE: DNA
<213> ORGANISM: Artificial Sequence
<220> FEATURE:
<223> OTHER INFORMATION: primer for inactivating nfrA

<400> SEQUENCE: 2
gacgtcttta ttgagtacca gcgcactcgc agacaatatc ggcaccagcg taggtgacac 60
tatagaacgc g 71

<210> SEQ ID NO 3
<211> LENGTH: 70
<212> TYPE: DNA
<213> ORGANISM: Artificial Sequence
<220> FEATURE:
<223> OTHER INFORMATION: primer for inactivating nfrA

<400> SEQUENCE: 3
aaccgttcgg gtgccattcg tcgctgtatt tgccgccatt aaagaatgag tagtggatct 60
gatgggtacc 70

<210> SEQ ID NO 4
<211> LENGTH: 70
<212> TYPE: DNA
<213> ORGANISM: Artificial Sequence
<220> FEATURE:
<223> OTHER INFORMATION: primer for inactivating nfrA

<400> SEQUENCE: 4
gcggatatat tgcgccgcat cgaggtacag gttttgggca aaccagcctg aaccgttcgg 60
gtgccattcg 70

<210> SEQ ID NO 5
<211> LENGTH: 20
<212> TYPE: DNA
<213> ORGANISM: Artificial Sequence
<220> FEATURE:
<223> OTHER INFORMATION: primer for inactivating nfrA

<400> SEQUENCE: 5
cgcgtcctga caattcaacg 20

<210> SEQ ID NO 6
<211> LENGTH: 20
<212> TYPE: DNA
<213> ORGANISM: Artificial Sequence
<220> FEATURE:
<223> OTHER INFORMATION: primer for inactivating nfrA

<400> SEQUENCE: 6
cgttgtcctg aacgtgagcg 20

<210> SEQ ID NO 7
<211> LENGTH: 70
<212> TYPE: DNA
<213> ORGANISM: Artificial Sequence
<220> FEATURE:
<223> OTHER INFORMATION: primer for inactivating nfrB

<400> SEQUENCE: 7
gtggactggc ttcttgatgt ttttgctacc tggctctacg gcttaaaagt aatcgcgata 60
acgttagcgg 70

<210> SEQ ID NO 8
<211> LENGTH: 70
<212> TYPE: DNA
<213> ORGANISM: Artificial Sequence
<220> FEATURE:
<223> OTHER INFORMATION: primer for inactivating nfrB

<400> SEQUENCE: 8
aatcgcgata acgttagcgg tcatcatgtt catcagcggg ctggacgatt taggtgacac 60
tatagaacgc 70

<210> SEQ ID NO 9
<211> LENGTH: 70
<212> TYPE: DNA
<213> ORGANISM: Artificial Sequence
<220> FEATURE:
<223> OTHER INFORMATION: primer for inactivating nfrB

<400> SEQUENCE: 9
aacctgcttt gagtaatagt gattgcatcg aaacttgtaa ttcgcgttga tagtggatct 60
gatgggtacc 70

<210> SEQ ID NO 10
<211> LENGTH: 70
<212> TYPE: DNA
<213> ORGANISM: Artificial Sequence
<220> FEATURE:
<223> OTHER INFORMATION: primer for inactivating nfrB

<400> SEQUENCE: 10
ttattctcct tcattttcgg actccagttg cgcaacctgt tctgtgttta aacctgcttt 60
gagtaatagt 70

<210> SEQ ID NO 11
<211> LENGTH: 20
<212> TYPE: DNA
<213> ORGANISM: Artificial Sequence
<220> FEATURE:
<223> OTHER INFORMATION: primer for inactivating nfrB

<400> SEQUENCE: 11
caatagtcat acctattaat 20

<210> SEQ ID NO 12
<211> LENGTH: 20
<212> TYPE: DNA
<213> ORGANISM: Artificial Sequence
<220> FEATURE:
<223> OTHER INFORMATION: primer for inactivating nfrB

<400> SEQUENCE: 12
ccccagctct tctgcgctgg 20

<210> SEQ ID NO 13
<211> LENGTH: 70
<212> TYPE: DNA
<213> ORGANISM: Artificial Sequence
<220> FEATURE:
<223> OTHER INFORMATION: primer for inactivating tsx

<400> SEQUENCE: 13
ggcgctctct tcgtctttta ctgtcaacgc agctgaaaac gacaaaccgc tagtggatct 60
gatgggtacc 70

<210> SEQ ID NO 14
<211> LENGTH: 70
<212> TYPE: DNA
<213> ORGANISM: Artificial Sequence
<220> FEATURE:
<223> OTHER INFORMATION: primer for inactivating tsx

<400> SEQUENCE: 14
cgttgaagtt gccgttgccg aagttcagtt ctgcatcgtc gttccactga taggtgacac 60
tatagaacgc 70

<210> SEQ ID NO 15
<211> LENGTH: 70
<212> TYPE: DNA
<213> ORGANISM: Artificial Sequence
<220> FEATURE:
<223> OTHER INFORMATION: primer for inactivating tsx

<400> SEQUENCE: 15
aacagtggca tacatatgaa aaaaacatta ctggcagccg gtgcggtact ggcgctctct 60
tcgtctttta 70

<210> SEQ ID NO 16
<211> LENGTH: 70
<212> TYPE: DNA
<213> ORGANISM: Artificial Sequence
<220> FEATURE:
<223> OTHER INFORMATION: primer for inactivating tsx

<400> SEQUENCE: 16
tcagaagttg taacctacta ccaggtaacc accccagccg gtagagcgaa cgttgaagtt 60
gccgttgccg 70

<210> SEQ ID NO 17
<211> LENGTH: 20
<212> TYPE: DNA
<213> ORGANISM: Artificial Sequence
<220> FEATURE:
<223> OTHER INFORMATION: primer for inactivating tsx

<400> SEQUENCE: 17
ttttataata ggctcctctg 20

<210> SEQ ID NO 18
<211> LENGTH: 18
<212> TYPE: DNA
<213> ORGANISM: Artificial Sequence
<220> FEATURE:
<223> OTHER INFORMATION: primer for inactivating tsx

<400> SEQUENCE: 18
gccggacaaa gcgtttac 18

<210> SEQ ID NO 19
<211> LENGTH: 21
<212> TYPE: DNA
<213> ORGANISM: Artificial Sequence
<220> FEATURE:
<223> OTHER INFORMATION: primer for inactivating fhuA

<400> SEQUENCE: 19
atggcgcgtt ccaaaactgc t 21

<210> SEQ ID NO 20
<211> LENGTH: 40
<212> TYPE: DNA
<213> ORGANISM: Artificial Sequence
<220> FEATURE:
<223> OTHER INFORMATION: primer for inactivating fhuA

<400> SEQUENCE: 20
cgcgttctat agtgtcacct cgtgtagcta agcgcttctt 40

<210> SEQ ID NO 21
<211> LENGTH: 40
<212> TYPE: DNA
<213> ORGANISM: Artificial Sequence
<220> FEATURE:
<223> OTHER INFORMATION: primer for inactivating fhuA

<400> SEQUENCE: 21
ggtacccatc agatccacta cttcgttgtg ggctgactac 40

<210> SEQ ID NO 22
<211> LENGTH: 21
<212> TYPE: DNA
<213> ORGANISM: Artificial Sequence
<220> FEATURE:
<223> OTHER INFORMATION: primer for inactivating fhuA

<400> SEQUENCE: 22
ttagaaacgg aaggttgcgg t 21

<210> SEQ ID NO 23
<211> LENGTH: 21
<212> TYPE: DNA
<213> ORGANISM: Artificial Sequence
<220> FEATURE:
<223> OTHER INFORMATION: primer for inactivating fhuA

<400> SEQUENCE: 23
gccgccagct gaagctttac c 21

<210> SEQ ID NO 24
<211> LENGTH: 20
<212> TYPE: DNA
<213> ORGANISM: Artificial Sequence
<220> FEATURE:
<223> OTHER INFORMATION: primer for inactivating fhuA

<400> SEQUENCE: 24
tagtggatct gatgggtacc 20

<210> SEQ ID NO 25

<211> LENGTH: 21
<212> TYPE: DNA
<213> ORGANISM: Artificial Sequence
<220> FEATURE:
<223> OTHER INFORMATION: primer for inactivating fhuA

<400> SEQUENCE: 25
cttcaggaac gctcagattg c 21

<210> SEQ ID NO 26
<211> LENGTH: 21
<212> TYPE: DNA
<213> ORGANISM: Artificial Sequence
<220> FEATURE:
<223> OTHER INFORMATION: primer for inactivating fhuA

<400> SEQUENCE: 26
cggaatgatt cgtgtattcc t 21

<210> SEQ ID NO 27
<211> LENGTH: 70
<212> TYPE: DNA
<213> ORGANISM: Artificial Sequence
<220> FEATURE:
<223> OTHER INFORMATION: primer for inactivating lamB

<400> SEQUENCE: 27
acgaccgaag ctgccgccgt tgaaatcagc aggaacggct ttgccgaagt tagtggatct 60
gatgggtacc 70

<210> SEQ ID NO 28
<211> LENGTH: 71
<212> TYPE: DNA
<213> ORGANISM: Artificial Sequence
<220> FEATURE:
<223> OTHER INFORMATION: primer for inactivating lamB

<400> SEQUENCE: 28
gtaatgtctg ctcaggcaat ggctgttgat ttccacggct atgcacgttc taggtgacac 60
tatagaacgc g 71

<210> SEQ ID NO 29
<211> LENGTH: 71
<212> TYPE: DNA
<213> ORGANISM: Artificial Sequence
<220> FEATURE:
<223> OTHER INFORMATION: primer for inactivating lamB

<400> SEQUENCE: 29
ttaccaccag atttccatct gggcaccgaa ggtccactcg tcgctgtcgc cacgaccgaa 60
gctgccgccg t 71

<210> SEQ ID NO 30
<211> LENGTH: 71
<212> TYPE: DNA
<213> ORGANISM: Artificial Sequence
<220> FEATURE:
<223> OTHER INFORMATION: primer for inactivating lamB

<400> SEQUENCE: 30
atgatgatta ctctgcgcaa acttcctctg gcggttgccg tcgcagcggg cgtaatgtct 60
gctcaggcaa t 71

```
<210> SEQ ID NO 31
<211> LENGTH: 20
<212> TYPE: DNA
<213> ORGANISM: Artificial Sequence
<220> FEATURE:
<223> OTHER INFORMATION: primer for inactivating lamB

<400> SEQUENCE: 31

cctacatttg acagccgttg                                              20


<210> SEQ ID NO 32
<211> LENGTH: 20
<212> TYPE: DNA
<213> ORGANISM: Artificial Sequence
<220> FEATURE:
<223> OTHER INFORMATION: primer for inactivating lamB

<400> SEQUENCE: 32

cacacaaagc ctgtcacagg                                              20


<210> SEQ ID NO 33
<211> LENGTH: 70
<212> TYPE: DNA
<213> ORGANISM: Artificial Sequence
<220> FEATURE:
<223> OTHER INFORMATION: primer for inactivating btuB

<400> SEQUENCE: 33

gtggttcaga aggtgtagct gccagacaag gtgtattccc gtcctgcagt tagtggatct     60

gatgggtacc                                                         70


<210> SEQ ID NO 34
<211> LENGTH: 70
<212> TYPE: DNA
<213> ORGANISM: Artificial Sequence
<220> FEATURE:
<223> OTHER INFORMATION: primer for inactivating btuB

<400> SEQUENCE: 34

gcccggatac tctcgtcgtt actgctaacc gttttgaaca gccgcgcagc taggtgacac     60

tatagaacgc                                                         70


<210> SEQ ID NO 35
<211> LENGTH: 70
<212> TYPE: DNA
<213> ORGANISM: Artificial Sequence
<220> FEATURE:
<223> OTHER INFORMATION: primer for inactivating btuB

<400> SEQUENCE: 35

gactccggcg tcggtgggtt gtcggtctat aaacaccagc acggtgggac gtggttcaga     60

aggtgtagct                                                         70


<210> SEQ ID NO 36
<211> LENGTH: 70
<212> TYPE: DNA
<213> ORGANISM: Artificial Sequence
<220> FEATURE:
<223> OTHER INFORMATION: primer for inactivating btuB

<400> SEQUENCE: 36

gctgacggcg tgttccgtca cggcattttc cgcttgggca caggatacca gcccggatac     60

tctcgtcgtt                                                         70
```

<210> SEQ ID NO 37
<211> LENGTH: 18
<212> TYPE: DNA
<213> ORGANISM: Artificial Sequence
<220> FEATURE:
<223> OTHER INFORMATION: primer for inactivating btuB

<400> SEQUENCE: 37
atctggttct catcatcg 18

<210> SEQ ID NO 38
<211> LENGTH: 20
<212> TYPE: DNA
<213> ORGANISM: Artificial Sequence
<220> FEATURE:
<223> OTHER INFORMATION: primer for inactivating btuB

<400> SEQUENCE: 38
gcataaatgt aatggagatc 20

<210> SEQ ID NO 39
<211> LENGTH: 2973
<212> TYPE: DNA
<213> ORGANISM: Escherichia coli

<400> SEQUENCE: 39
atgaaggaga ataaccttaa tcgcgtcatc ggatggtctg gtttactgct gacgtcttta 60
ttgagtacca gcgcactcgc agacaatatc ggcaccagcg cagaagagct ggggctgagc 120
gattatcgcc attttgttat ttatccccgt ctcgataaag cgctgaaggc acagaaaaat 180
aacgacgaag caaccgccat ccgcgaattt gaatatatac accagcaggt gccggataat 240
attccgctga ctttatacct tgcggaagcc tatcgccatt ttggtcatga tgaccgggcg 300
cggctgttgc ttgaggatca actgaaacgt cacccaggag atgcccgact tgagcgcagt 360
ctggcggcta ttccggttga agtgaaaagc gttacgacag ttgaagaact gcttgcccag 420
caaaaagcgt gcgatgctgc gccgaccctg cgttgtcgca gtgaagtcgg gcagaatgcc 480
ctgcggctgg cacagttacc tgtcgccaga gcgcaactga acgatgcgac gtttgctgca 540
tcgccggaag gaaaaacgct gcgaaccgat ctgctgcaac gggcaatcta cctgaaacaa 600
tggtcccagg cagatacgct atacaatgaa gcacgccagc agaacacatt aagcgcggca 660
gaacgccgtc agtggtttga cgtgcttctt gccgggcagc tggacgatcg gatcctggca 720
ctgcaatcac aggggatctt caccgatcct cagtcatata ttacttacgc gaccgcgctg 780
gcttatcgtg gcgaaaaagc acgcctccag cattatctca ttgaaaataa gccactattt 840
accacggacg cacaagagaa aagttggctc tatctgttat ctaaatacag cgctaacccc 900
gttcaggcgt tggcgaatta tacggtacag tttgccgaca accgccagta tgttgttggc 960
gcgacgctac cggtgctgtt aaaagaaggt cagtacgacg cagcgcaaaa actgctcgcc 1020
accctccccg ccaatgaaat gcttgaggag cgttatgctg tcagcgtggc gacccgtaac 1080
aaggctgaag ctctgcgtct ggcacgattg ctgtatcagc aagaaccggc aaatcttacc 1140
cgcctggatc aactaacctg gcaactgatg cagaacgagc agtcacgcga agctgccgat 1200
ttattgctgc aacgctatcc tttccagggc gatgcgcgtg tcagccagac tttaatggcg 1260
cgactggcgt ctctgctgga aagtcatcct tacctggcaa cgccggcgaa ggtggcgatt 1320
ttatcgaaac ccttaccgct ggcggagcaa cgtcagtggc aaagtcagtt gccgggtatt 1380
gcagataatt gcccggcaat agttcgcttg ctgggcgata tgtcgccttc ctacgatgcc 1440

```
gccgcctgga accgtctggc aaagtgttat cgggacacgc tacccggtgt ggcgttgtat   1500

gcatggcttc aggccgaaca acgacaaccg agcgcctggc aacatcgtgc ggtagcctat   1560

caggcgtatc aggttgagga ctacgccacc gcactggcgg cctggcagaa aatcagtctt   1620

cacgacatga gcaatgagga tctgcttgct gctgccaata ccgcccaggc ggcaggaaat   1680

ggtgcggctc gcgatcgctg gctacaacag gcagaaaaac gtggactggg aagcaatgcc   1740

ctctactggt ggctgcatgc gcaacgttac attcctggtc agccggaact cgcactgaac   1800

gatctcacgc gctcaatcaa tattgcgcct tctgccaacg cttacgttgc gcgggcgaca   1860

atttatcgcc aacgtcataa tgtcccggcc gcggtgagtg atttgcgcgc cgcgctggaa   1920

ctggaaccga ataatagcaa cacccaggca gcgcttggtt acgccttgtg ggatagcggt   1980

gatatcgcac agtcgcggga aatgctcgaa ccggcgcata aagggcttcc ggacgatccg   2040

gcactgatcc gacaactggc ctacgtgaac cagcgtctgg atgacatgcc tgcgacgcag   2100

cactacgccc ggctggtgat tgatgacatt gataatcagg cgctgataac cccactgacc   2160

ccagaacaaa atcaacaacg cttcaatttc cgccgtttgc atgaggaggt cggtcgccgc   2220

tggacgttca gtttcgattc ttccatcggc ttgcgttccg gcgcaatgag taccgctaac   2280

aataatgtcg gcggcgcagc gccagggaaa agctatcgta gctacggaca actggaagcc   2340

gagtaccgca tcggacgcaa tatgctgctg gaaggcgacc tgctctcagt ttatagccgc   2400

gtctttgccg ataccggaga aaacggggtg atgatgccgg tgaaaaatcc gatgtccggc   2460

accggtctgc gctggaagcc gctgcgcgat cagatctttt tcatcgccgt cgaacagcag   2520

ttgccgctga acggccaaaa tggcgcatcc gataccatgc tgcgcgccag cgcctcattc   2580

tttaatggcg gcaaatacag cgacgaatgg cacccgaacg gttcaggctg gtttgcccaa   2640

aacctgtacc tcgatgcggc gcaatatatc cgccaggata ttcaggcgtg gacggcagat   2700

tatcgcgtca gctggcatca gaaggtagct aacggacaga ctattgagcc ttacgctcac   2760

gttcaggaca acggctatcg tgataaaggc actcagggcg cgcagcttgg cggagtcggg   2820

gtccgctgga atatctggac cggcgagacg cactacgacg cctggccgca caaagtcagt   2880

ctcggcgtcg agtatcaaca taccttttaag gcgattaatc aacgtaacgg agagcgcaac   2940

aacgcgtttc tcaccattgg agtgcactgg taa                               2973
```

<210> SEQ ID NO 40
<211> LENGTH: 990
<212> TYPE: PRT
<213> ORGANISM: Escherichia coli

<400> SEQUENCE: 40

```
Met Lys Glu Asn Asn Leu Asn Arg Val Ile Gly Trp Ser Gly Leu Leu
1               5                   10                  15

Leu Thr Ser Leu Leu Ser Thr Ser Ala Leu Ala Asp Asn Ile Gly Thr
            20                  25                  30

Ser Ala Glu Glu Leu Gly Leu Ser Asp Tyr Arg His Phe Val Ile Tyr
        35                  40                  45

Pro Arg Leu Asp Lys Ala Leu Lys Ala Gln Lys Asn Asn Asp Glu Ala
    50                  55                  60

Thr Ala Ile Arg Glu Phe Glu Tyr Ile His Gln Gln Val Pro Asp Asn
65                  70                  75                  80

Ile Pro Leu Thr Leu Tyr Leu Ala Glu Ala Tyr Arg His Phe Gly His
                85                  90                  95
```

-continued

```
Asp Asp Arg Ala Arg Leu Leu Leu Glu Asp Gln Leu Lys Arg His Pro
            100                 105                 110

Gly Asp Ala Arg Leu Glu Arg Ser Leu Ala Ala Ile Pro Val Glu Val
        115                 120                 125

Lys Ser Val Thr Thr Val Glu Glu Leu Leu Ala Gln Gln Lys Ala Cys
    130                 135                 140

Asp Ala Ala Pro Thr Leu Arg Cys Arg Ser Glu Val Gly Gln Asn Ala
145                 150                 155                 160

Leu Arg Leu Ala Gln Leu Pro Val Ala Arg Ala Gln Leu Asn Asp Ala
                165                 170                 175

Thr Phe Ala Ala Ser Pro Glu Gly Lys Thr Leu Arg Thr Asp Leu Leu
            180                 185                 190

Gln Arg Ala Ile Tyr Leu Lys Gln Trp Ser Gln Ala Asp Thr Leu Tyr
        195                 200                 205

Asn Glu Ala Arg Gln Gln Asn Thr Leu Ser Ala Ala Glu Arg Arg Gln
    210                 215                 220

Trp Phe Asp Val Leu Leu Ala Gly Gln Leu Asp Asp Arg Ile Leu Ala
225                 230                 235                 240

Leu Gln Ser Gln Gly Ile Phe Thr Asp Pro Gln Ser Tyr Ile Thr Tyr
                245                 250                 255

Ala Thr Ala Leu Ala Tyr Arg Gly Glu Lys Ala Arg Leu Gln His Tyr
            260                 265                 270

Leu Ile Glu Asn Lys Pro Leu Phe Thr Thr Asp Ala Gln Glu Lys Ser
        275                 280                 285

Trp Leu Tyr Leu Leu Ser Lys Tyr Ser Ala Asn Pro Val Gln Ala Leu
    290                 295                 300

Ala Asn Tyr Thr Val Gln Phe Ala Asp Asn Arg Gln Tyr Val Val Gly
305                 310                 315                 320

Ala Thr Leu Pro Val Leu Leu Lys Glu Gly Gln Tyr Asp Ala Ala Gln
                325                 330                 335

Lys Leu Leu Ala Thr Leu Pro Ala Asn Glu Met Leu Glu Glu Arg Tyr
            340                 345                 350

Ala Val Ser Val Ala Thr Arg Asn Lys Ala Glu Ala Leu Arg Leu Ala
        355                 360                 365

Arg Leu Leu Tyr Gln Gln Glu Pro Ala Asn Leu Thr Arg Leu Asp Gln
    370                 375                 380

Leu Thr Trp Gln Leu Met Gln Asn Glu Gln Ser Arg Glu Ala Ala Asp
385                 390                 395                 400

Leu Leu Leu Gln Arg Tyr Pro Phe Gln Gly Asp Ala Arg Val Ser Gln
                405                 410                 415

Thr Leu Met Ala Arg Leu Ala Ser Leu Leu Glu Ser His Pro Tyr Leu
            420                 425                 430

Ala Thr Pro Ala Lys Val Ala Ile Leu Ser Lys Pro Leu Pro Leu Ala
        435                 440                 445

Glu Gln Arg Gln Trp Gln Ser Gln Leu Pro Gly Ile Ala Asp Asn Cys
    450                 455                 460

Pro Ala Ile Val Arg Leu Leu Gly Asp Met Ser Pro Ser Tyr Asp Ala
465                 470                 475                 480

Ala Ala Trp Asn Arg Leu Ala Lys Cys Tyr Arg Asp Thr Leu Pro Gly
                485                 490                 495

Val Ala Leu Tyr Ala Trp Leu Gln Ala Glu Gln Arg Gln Pro Ser Ala
            500                 505                 510

Trp Gln His Arg Ala Val Ala Tyr Gln Ala Tyr Gln Val Glu Asp Tyr
```

```
        515                 520                 525

Ala Thr Ala Leu Ala Ala Trp Gln Lys Ile Ser Leu His Asp Met Ser
    530                 535                 540

Asn Glu Asp Leu Leu Ala Ala Ala Asn Thr Ala Gln Ala Ala Gly Asn
545                 550                 555                 560

Gly Ala Ala Arg Asp Arg Trp Leu Gln Gln Ala Glu Lys Arg Gly Leu
                565                 570                 575

Gly Ser Asn Ala Leu Tyr Trp Trp Leu His Ala Gln Arg Tyr Ile Pro
            580                 585                 590

Gly Gln Pro Glu Leu Ala Leu Asn Asp Leu Thr Arg Ser Ile Asn Ile
        595                 600                 605

Ala Pro Ser Ala Asn Ala Tyr Val Ala Arg Ala Thr Ile Tyr Arg Gln
    610                 615                 620

Arg His Asn Val Pro Ala Ala Val Ser Asp Leu Arg Ala Ala Leu Glu
625                 630                 635                 640

Leu Glu Pro Asn Asn Ser Asn Thr Gln Ala Ala Leu Gly Tyr Ala Leu
                645                 650                 655

Trp Asp Ser Gly Asp Ile Ala Gln Ser Arg Glu Met Leu Glu Pro Ala
            660                 665                 670

His Lys Gly Leu Pro Asp Asp Pro Ala Leu Ile Arg Gln Leu Ala Tyr
        675                 680                 685

Val Asn Gln Arg Leu Asp Asp Met Pro Ala Thr Gln His Tyr Ala Arg
    690                 695                 700

Leu Val Ile Asp Asp Ile Asp Asn Gln Ala Leu Ile Thr Pro Leu Thr
705                 710                 715                 720

Pro Glu Gln Asn Gln Gln Arg Phe Asn Phe Arg Arg Leu His Glu Glu
                725                 730                 735

Val Gly Arg Arg Trp Thr Phe Ser Phe Asp Ser Ser Ile Gly Leu Arg
            740                 745                 750

Ser Gly Ala Met Ser Thr Ala Asn Asn Asn Val Gly Gly Ala Ala Pro
        755                 760                 765

Gly Lys Ser Tyr Arg Ser Tyr Gly Gln Leu Glu Ala Glu Tyr Arg Ile
    770                 775                 780

Gly Arg Asn Met Leu Leu Glu Gly Asp Leu Leu Ser Val Tyr Ser Arg
785                 790                 795                 800

Val Phe Ala Asp Thr Gly Glu Asn Gly Val Met Met Pro Val Lys Asn
                805                 810                 815

Pro Met Ser Gly Thr Gly Leu Arg Trp Lys Pro Leu Arg Asp Gln Ile
            820                 825                 830

Phe Phe Ile Ala Val Glu Gln Gln Leu Pro Leu Asn Gly Gln Asn Gly
        835                 840                 845

Ala Ser Asp Thr Met Leu Arg Ala Ser Ala Ser Phe Phe Asn Gly Gly
    850                 855                 860

Lys Tyr Ser Asp Glu Trp His Pro Asn Gly Ser Gly Trp Phe Ala Gln
865                 870                 875                 880

Asn Leu Tyr Leu Asp Ala Ala Gln Tyr Ile Arg Gln Asp Ile Gln Ala
                885                 890                 895

Trp Thr Ala Asp Tyr Arg Val Ser Trp His Gln Lys Val Ala Asn Gly
            900                 905                 910

Gln Thr Ile Glu Pro Tyr Ala His Val Gln Asp Asn Gly Tyr Arg Asp
        915                 920                 925

Lys Gly Thr Gln Gly Ala Gln Leu Gly Gly Val Gly Val Arg Trp Asn
    930                 935                 940
```

```
Ile Trp Thr Gly Glu Thr His Tyr Asp Ala Trp Pro His Lys Val Ser
945                 950                 955                 960

Leu Gly Val Glu Tyr Gln His Thr Phe Lys Ala Ile Asn Gln Arg Asn
                965                 970                 975

Gly Glu Arg Asn Asn Ala Phe Leu Thr Ile Gly Val His Trp
            980                 985                 990


<210> SEQ ID NO 41
<211> LENGTH: 2238
<212> TYPE: DNA
<213> ORGANISM: Escherichia coli

<400> SEQUENCE: 41

gtggactggc ttcttgatgt ttttgctacc tggctctacg gcttaaaagt aatcgcgata      60

acgttagcgg tcatcatgtt catcagcggg ctggacgatt tttttattga tgtcgtctac     120

tgggtacgcc gcattaaacg caagttgagt gtttatcgcc gctacccgcg aatgagttac     180

cgcgaactgt ataaaccaga tgaaaaaccg ttagcgatta tggttccggc gtggaatgaa     240

acgggcgtca tcggcaatat ggccgagctg gcggcgacca cgctcgacta cgaaaactat     300

catatctttg ttggcaccta ccccaacgac cccgatactc agcgtgatgt tgacgaagtg     360

tgcgctcgct tcccgaatgt gcataaggta gtctgcgcgc gtcctggccc caccagcaaa     420

gccgactgtc tgaacaacgt gctggacgcc atcacccaat ttgagcgtag cgccaatttc     480

gcttttgctg gttttattct gcatgacgcc gaagatgtga tttcaccgat ggaattgcgt     540

ctgttcaact atctggtcga gcgtaaagat ctgattcaga tcccggtgta tccgttcgaa     600

cgcgaatgga cgcacttcac cagcatgact tacattgatg agttttcaga gctgcatggc     660

aaagatgttc cggtgcgtga agccctcgcc ggacaagtgc ccagcgcagg cgtcggcacc     720

tgtttcagcc gccgcgccgt gaccgcactg ttagctgacg gtgacggtat tgctttcgac     780

gtgcagagtc ttactgaaga ttacgacatt ggcttccgcc tgaaagaaaa aggtatgacg     840

gaaatttttg tccgttttcc ggtggtggac gaagccaaag aacgcgagca gcgtaaattt     900

ttacagcacg cgcggacatc aaacatgatc tgcgtgcgcg aatatttccc cgataccttt     960

tcgactgcgg ttcgacaaaa atcccgctgg atcatcggca ttgttttcca aggctttaaa    1020

acccataaat ggacctccag cctgacgctg aactactttc tctggcgcga ccgcaaaggg    1080

gcaatcagta actttgtcag cttcctcgcg atgctggtga tgatccagct tttgctgttg    1140

ctggcgtatg aaagtttgtg gcccgatgcc tggcatttcc tttctatttt cagcggcagc    1200

gcatggttaa tgaccctgct gtggctaaac tttggtttga tggttaaccg catcgtgcag    1260

cgggtgattt tcgttactgg ctactacggc ctgacgcagg ggctgctttc cgtcctgcgt    1320

cttttctggg gcaacctgat taacttcatg gccaactggc gcgcgctaaa acaggtactt    1380

caacacggcg atccacgtcg cgtggcgtgg gataaaacaa cgcatgactt ccccagcgtg    1440

actggcgata cccgctcgtt gcgcccgtta ggtcaaattc tgctggaaaa tcaggtcatc    1500

actgaagaac aactcgatac agcactgcgt aatcgcgtcg aaggtctacg cctgggcggt    1560

tcaatgctga tgcaggggct gattagcgcc gagcagctgg cacaggcgct ggcagagcaa    1620

aacggcgtgg cgtgggaatc catcgatgcc tggcagatcc cttcctcgct gattgccgaa    1680

atgccggcct ccgtggcgct gcattatgcg gtactgccgc tgcgtctgga aaatgacgag    1740

ttaattgtcg gcagtgaaga tggtattgac ccggtttcgc tggcggccct gacgcgtaaa    1800

gtcggacgca aagtgcgtta cgtcattgtt ctgcggggac aaattgtcac agggttacgt    1860
```

```
cactggtatg cacgccgacg cggtcacgat ccgcgggcaa tgttgtacaa tgcggttcag   1920

catcagtggc tcacggaaca gcaggccggt gaaatctggc ggcaatatgt gccgcatcag   1980

ttcctgttcg ccgaaatact gaccacgctc ggtcatatta atcgttcagc aattaacgtg   2040

ttgttattgc gccatgaacg cagttctctg ccgctcggca agtttttggt caccgaaggc   2100

gttatcagcc aggaaacgtt ggatcgcgtc ctgacaattc aacgcgaatt acaagtttcg   2160

atgcaatcac tattactcaa agcaggttta aacacagaac aggttgcgca actggagtcc   2220

gaaaatgaag gagaataa                                                 2238
```

```
<210> SEQ ID NO 42
<211> LENGTH: 745
<212> TYPE: PRT
<213> ORGANISM: Escherichia coli

<400> SEQUENCE: 42

Met Asp Trp Leu Leu Asp Val Phe Ala Thr Trp Leu Tyr Gly Leu Lys
1               5                   10                  15

Val Ile Ala Ile Thr Leu Ala Val Ile Met Phe Ile Ser Gly Leu Asp
            20                  25                  30

Asp Phe Phe Ile Asp Val Val Tyr Trp Val Arg Arg Ile Lys Arg Lys
        35                  40                  45

Leu Ser Val Tyr Arg Arg Tyr Pro Arg Met Ser Tyr Arg Glu Leu Tyr
    50                  55                  60

Lys Pro Asp Glu Lys Pro Leu Ala Ile Met Val Pro Ala Trp Asn Glu
65                  70                  75                  80

Thr Gly Val Ile Gly Asn Met Ala Glu Leu Ala Ala Thr Thr Leu Asp
                85                  90                  95

Tyr Glu Asn Tyr His Ile Phe Val Gly Thr Tyr Pro Asn Asp Pro Asp
            100                 105                 110

Thr Gln Arg Asp Val Asp Glu Val Cys Ala Arg Phe Pro Asn Val His
        115                 120                 125

Lys Val Val Cys Ala Arg Pro Gly Pro Thr Ser Lys Ala Asp Cys Leu
    130                 135                 140

Asn Asn Val Leu Asp Ala Ile Thr Gln Phe Glu Arg Ser Ala Asn Phe
145                 150                 155                 160

Ala Phe Ala Gly Phe Ile Leu His Asp Ala Glu Asp Val Ile Ser Pro
                165                 170                 175

Met Glu Leu Arg Leu Phe Asn Tyr Leu Val Glu Arg Lys Asp Leu Ile
            180                 185                 190

Gln Ile Pro Val Tyr Pro Phe Glu Arg Glu Trp Thr His Phe Thr Ser
        195                 200                 205

Met Thr Tyr Ile Asp Glu Phe Ser Glu Leu His Gly Lys Asp Val Pro
    210                 215                 220

Val Arg Glu Ala Leu Ala Gly Gln Val Pro Ser Ala Gly Val Gly Thr
225                 230                 235                 240

Cys Phe Ser Arg Arg Ala Val Thr Ala Leu Leu Ala Asp Gly Asp Gly
                245                 250                 255

Ile Ala Phe Asp Val Gln Ser Leu Thr Glu Asp Tyr Asp Ile Gly Phe
            260                 265                 270

Arg Leu Lys Glu Lys Gly Met Thr Glu Ile Phe Val Arg Phe Pro Val
        275                 280                 285

Val Asp Glu Ala Lys Glu Arg Glu Gln Arg Lys Phe Leu Gln His Ala
    290                 295                 300
```

```
Arg Thr Ser Asn Met Ile Cys Val Arg Glu Tyr Phe Pro Asp Thr Phe
305                 310                 315                 320

Ser Thr Ala Val Arg Gln Lys Ser Arg Trp Ile Ile Gly Ile Val Phe
                325                 330                 335

Gln Gly Phe Lys Thr His Lys Trp Thr Ser Ser Leu Thr Leu Asn Tyr
            340                 345                 350

Phe Leu Trp Arg Asp Arg Lys Gly Ala Ile Ser Asn Phe Val Ser Phe
        355                 360                 365

Leu Ala Met Leu Val Met Ile Gln Leu Leu Leu Leu Leu Ala Tyr Glu
    370                 375                 380

Ser Leu Trp Pro Asp Ala Trp His Phe Leu Ser Ile Phe Ser Gly Ser
385                 390                 395                 400

Ala Trp Leu Met Thr Leu Leu Trp Leu Asn Phe Gly Leu Met Val Asn
                405                 410                 415

Arg Ile Val Gln Arg Val Ile Phe Val Thr Gly Tyr Tyr Gly Leu Thr
            420                 425                 430

Gln Gly Leu Leu Ser Val Leu Arg Leu Phe Trp Gly Asn Leu Ile Asn
        435                 440                 445

Phe Met Ala Asn Trp Arg Ala Leu Lys Gln Val Leu Gln His Gly Asp
    450                 455                 460

Pro Arg Arg Val Ala Trp Asp Lys Thr Thr His Asp Phe Pro Ser Val
465                 470                 475                 480

Thr Gly Asp Thr Arg Ser Leu Arg Pro Leu Gly Gln Ile Leu Leu Glu
                485                 490                 495

Asn Gln Val Ile Thr Glu Glu Gln Leu Asp Thr Ala Leu Arg Asn Arg
            500                 505                 510

Val Glu Gly Leu Arg Leu Gly Gly Ser Met Leu Met Gln Gly Leu Ile
        515                 520                 525

Ser Ala Glu Gln Leu Ala Gln Ala Leu Ala Glu Gln Asn Gly Val Ala
    530                 535                 540

Trp Glu Ser Ile Asp Ala Trp Gln Ile Pro Ser Ser Leu Ile Ala Glu
545                 550                 555                 560

Met Pro Ala Ser Val Ala Leu His Tyr Ala Val Leu Pro Leu Arg Leu
                565                 570                 575

Glu Asn Asp Glu Leu Ile Val Gly Ser Glu Asp Gly Ile Asp Pro Val
            580                 585                 590

Ser Leu Ala Ala Leu Thr Arg Lys Val Gly Arg Lys Val Arg Tyr Val
        595                 600                 605

Ile Val Leu Arg Gly Gln Ile Val Thr Gly Leu Arg His Trp Tyr Ala
    610                 615                 620

Arg Arg Arg Gly His Asp Pro Arg Ala Met Leu Tyr Asn Ala Val Gln
625                 630                 635                 640

His Gln Trp Leu Thr Glu Gln Gln Ala Gly Glu Ile Trp Arg Gln Tyr
                645                 650                 655

Val Pro His Gln Phe Leu Phe Ala Glu Ile Leu Thr Thr Leu Gly His
            660                 665                 670

Ile Asn Arg Ser Ala Ile Asn Val Leu Leu Leu Arg His Glu Arg Ser
        675                 680                 685

Ser Leu Pro Leu Gly Lys Phe Leu Val Thr Glu Gly Val Ile Ser Gln
    690                 695                 700

Glu Thr Leu Asp Arg Val Leu Thr Ile Gln Arg Glu Leu Gln Val Ser
705                 710                 715                 720
```

```
Met Gln Ser Leu Leu Leu Lys Ala Gly Leu Asn Thr Glu Gln Val Ala
                725                 730                 735

Gln Leu Glu Ser Glu Asn Glu Gly Glu
            740                 745


<210> SEQ ID NO 43
<211> LENGTH: 6088
<212> TYPE: DNA
<213> ORGANISM: Escherichia coli

<400> SEQUENCE: 43

gtggactggc ttcttgatgt ttttgctacc tggctctacg gcttaaaagt aatcgcgata     60

acgttagcgg tcatcatgtt catcagcggg ctggacgatt tttttattga tgtcgtctac    120

tgggtacgcc gcattaaacg caagttgagt gtttatcgcc gctacccgcg aatgagttac    180

cgcgaactgt ataaaccaga tgaaaaaccg ttagcgatta tggttccggc gtggaatgaa    240

acgggcgtca tcggcaatat ggccgagctg gcggcgacca cgctcgacta cgaaaactat    300

catatctttg ttggcaccta ccccaacgac cccgatactc agcgtgatgt tgacgaagtg    360

tgcgctcgct tcccgaatgt gcataaggta gtctgcgcgc gtcctggccc caccagcaaa    420

gccgactgtc tgaacaacgt gctggacgcc atcacccaat ttgagcgtag cgccaatttc    480

gcttttgctg gttttattct gcatgacgcc gaagatgtga tttcaccgat ggaattgcgt    540

ctgttcaact atctggtcga gcgtaaagat ctgattcaga tcccggtgta tccgttcgaa    600

cgcgaatgga cgcacttcac cagcatgact tacattgatg agttttcaga gctgcatggc    660

aaagatgttc cggtgcgtga agccctcgcc ggacaagtgc ccagcgcagg cgtcggcacc    720

tgtttcagcc gccgcgccgt gaccgcactg ttagctgacg gtgacggtat tgctttcgac    780

gtgcagagtc ttactgaaga ttacgacatt ggcttccgcc tgaaagaaaa aggtatgacg    840

gaaatttttg tccgttttcc ggtggtggac gaagccaaag aacgcgagca gcgtaaattt    900

ttacagcacg cgcggacatc aaacatgatc tgcgtgcgcg aatatttccc cgataccttt    960

tcgactgcgg ttcgacaaaa atcccgctgg atcatcggca ttgttttcca aggctttaaa   1020

acccataaat ggacctccag cctgacgctg aactactttc tctggcgcga ccgcaaaggg   1080

gcaatcagta actttgtcag cttcctcgcg atgctggtga tgatccagct tttgctgttg   1140

ctggcgtatg aaagtttgtg gcccgatgcc tggcatttcc tttctatttt cagcggcagc   1200

gcatggttaa tgaccctgct gtggctaaac tttggtttga tggttaaccg catcgtgcag   1260

cgggtgattt tcgttactgg ctactacggc ctgacgcagg ggctgctttc cgtcctgcgt   1320

cttttctggg gcaacctgat taacttcatg gccaactggc gcgcgctaaa acaggtactt   1380

caacacggcg atccacgtcg cgtggcgtgg gataaaacaa cgcatgactt ccccagcgtg   1440

actggcgata cccgctcgtt gcgcccgtta ggtcaaattc tgctggaaaa tcaggtcatc   1500

actgaagaac aactcgatac agcactgcgt aatcgcgtcg aaggtctacg cctgggcggt   1560

tcaatgctga tgcaggggct gattagcgcc gagcagctgg cacaggcgct ggcagagcaa   1620

aacggcgtgg cgtgggaatc catcgatgcc tggcagatcc cttcctcgct gattgccgaa   1680

atgccggcct ccgtggcgct gcattatgcg gtactgccgc tgcgtctgga aaatgacgag   1740

ttaattgtcg gcagtgaaga tggtattgac ccggtttcgc tggcggccct gacgcgtaaa   1800

gtcggacgca aagtgcgtta cgtcattgtt ctgcggggac aaattgtcac agggttacgt   1860

cactggtatg cacgccgacg cggtcacgat ccgcgggcaa tgttgtacaa tgcggttcag   1920

catcagtggc tcacggaaca gcaggccggt gaaatctggc ggcaatatgt gccgcatcag   1980
```

-continued

```
ttcctgttcg ccgaaatact gaccacgctc ggtcatatta atcgttcagc aattaacgtg   2040

ttgttattgc gccatgaacg cagttctctg ccgctcggca agtttttggt caccgaaggc   2100

gttatcagcc aggaaacgtt ggatcgcgtc ctgacaattc aacgcgaatt acaagtttcg   2160

atgcaatcac tattactcaa agcaggttta aacacagaac aggttgcgca actggagtcc   2220

gaaaatgaag gagaataacc ttaatcgcgt catcggatgg tctggtttac tgctgacgtc   2280

tttattgagt accagcgcac tcgcagacaa tatcggcacc agcgcagaag agctggggct   2340

gagcgattat cgccattttg ttatttatcc ccgtctcgat aaagcgctga aggcacagaa   2400

aaataacgac gaagcaaccg ccatccgcga atttgaatat atacaccagc aggtgccgga   2460

taatattccg ctgactttat accttgcgga agcctatcgc cattttggtc atgatgaccg   2520

ggcgcggctg ttgcttgagg atcaactgaa acgtcaccca ggagatgccc gacttgagcg   2580

cagtctggcg gctattccgg ttgaagtgaa aagcgttacg acagttgaag aactgcttgc   2640

ccagcaaaaa gcgtgcgatg ctgcgccgac cctgcgttgt cgcagtgaag tcgggcagaa   2700

tgccctgcgg ctggcacagt tacctgtcgc cagagcgcaa ctgaacgatg cgacgtttgc   2760

tgcatcgccg gaaggaaaaa cgctgcgaac cgatctgctg caacgggcaa tctacctgaa   2820

acaatggtcc caggcagata cgctatacaa tgaagcacgc cagcagaaca cattaagcgc   2880

ggcagaacgc cgtcagtggt ttgacgtgct tcttgccggg cagctggacg atcggatcct   2940

ggcactgcaa tcacagggga tcttcaccga tcctcagtca tatattactt acgcgaccgc   3000

gctggcttat cgtggcgaaa aagcacgcct ccagcattat ctcattgaaa ataagccact   3060

atttaccacg gacgcacaag agaaaagttg gctctatctg ttatctaaat acagcgctaa   3120

ccccgttcag gcgttggcga attatacggt acagtttgcc gacaaccgcc agtatgttgt   3180

tggcgcgacg ctaccggtgc tgttaaaaga aggtcagtac gacgcagcgc aaaaactgct   3240

cgccaccctc cccgccaatg aaatgcttga ggagcgttat gctgtcagcg tggcgacccg   3300

taacaaggct gaagctctgc gtctggcacg attgctgtat cagcaagaac cggcaaatct   3360

tacccgcctg gatcaactaa cctggcaact gatgcagaac gagcagtcac gcgaagctgc   3420

cgatttattg ctgcaacgct atcctttcca gggcgatgcg cgtgtcagcc agactttaat   3480

ggcgcgactg gcgtctctgc tggaaagtca tccttacctg gcaacgccgg cgaaggtggc   3540

gattttatcg aaacccttac cgctggcgga gcaacgtcag tggcaaagtc agttgccggg   3600

tattgcagat aattgcccgg caatagttcg cttgctgggc gatatgtcgc cttcctacga   3660

tgccgccgcc tggaaccgtc tggcaaagtg ttatcgggac acgctacccg gtgtggcgtt   3720

gtatgcatgg cttcaggccg aacaacgaca accgagcgcc tggcaacatc gtgcggtagc   3780

ctatcaggcg tatcaggttg aggactacgc caccgcactg gcggcctggc agaaaatcag   3840

tcttcacgac atgagcaatg aggatctgct tgctgctgcc aataccgccc aggcggcagg   3900

aaatggtgcg gctcgcgatc gctggctaca acaggcagaa aaacgtggac tgggaagcaa   3960

tgccctctac tggtggctgc atgcgcaacg ttacattcct ggtcagccgg aactcgcact   4020

gaacgatctc acgcgctcaa tcaatattgc gccttctgcc aacgcttacg ttgcgcgggc   4080

gacaatttat cgccaacgtc ataatgtccc ggccgcggtg agtgatttgc gcgccgcgct   4140

ggaactggaa ccgaataata gcaacaccca ggcagcgctt ggttacgcct tgtgggatag   4200

cggtgatatc gcacagtcgc gggaaatgct cgaaccggcg cataaagggc ttccggacga   4260

tccggcactg atccgacaac tggcctacgt gaaccagcgt ctggatgaca tgcctgcgac   4320
```

gcagcactac gcccggctgg tgattgatga cattgataat caggcgctga taacccccact 4380 gaccccagaa caaaatcaac aacgcttcaa tttccgccgt ttgcatgagg aggtcggtcg 4440
ccgctggacg ttcagtttcg attcttccat cggcttgcgt tccggcgcaa tgagtaccgc 4500
taacaataat gtcggcggcg cagcgccagg gaaaagctat cgtagctacg gacaactgga 4560
agccgagtac cgcatcggac gcaatatgct gctggaaggc gacctgctct cagtttatag 4620
ccgcgtcttt gccgataccg gagaaaacgg ggtgatgatg ccggtgaaaa atccgatgtc 4680
cggcaccggt ctgcgctgga agccgctgcg cgatcagatc tttttcatcg ccgtcgaaca 4740
gcagttgccg ctgaacggcc aaaatggcgc atccgatacc atgctgcgcg ccagcgcctc 4800
attctttaat ggcggcaaat acagcgacga atggcacccg aacggttcag gctggtttgc 4860
ccaaaacctg tacctcgatg cggcgcaata tatccgccag gatattcagg cgtggacggc 4920
agattatcgc gtcagctggc atcagaaggt agctaacgga cagactattg agccttacgc 4980
tcacgttcag gacaacggct atcgtgataa aggcactcag ggcgcgcagc ttggcggagt 5040
cggggtccgc tggaatatct ggaccggcga gacgcactac gacgcctggc cgcacaaagt 5100
cagtctcggc gtcgagtatc aacatacctt taaggcgatt aatcaacgta acggagagcg 5160
caacaacgcg tttctcacca ttggagtgca ctggtaaatg cgtaagttca ttttcgtatt 5220
gctgacactg cttttggtca gcccttttc ctttgcgatg aaaggtatta tctggcaacc 5280
acaaaaccga gatagtcagg ttaccgatac ccagtggcag gggctgatga gtcagttacg 5340
tttgcaaggc ttcgataccc ttgttttgca atggacccgt tacggcgatg catttaccca 5400
gccagaacag cgcacgttat tgtttaagcg ggccgcagct gcgcaacagg ctggtctgaa 5460
gcttattgtc gggctgaacg ccgatccgga atttttatg caccagaaac agtcgtccgc 5520
agcgctggaa agctatctta atcgcctgct ggctgccgat ctccagcaag ccagattatg 5580
gagcgccgcg cctggcataa cgccggatgg ctggtacatc agcgcggaaa ttgacgacct 5640
gaactggcgc agcgaagccg cccgtcagcc tttgctaaca tggttaaaca acgcgcagcg 5700
gctgattagc gatgtttcag caaaaccggt ttatatcagt agtttttcg ccggaaacat 5760 gtcgcccgat ggctatcgcc aactgctgga acacgttaaa gcaaccggcg ttaatgtctg 5820
ggtacaggat ggcagcggcg tggataaact gaccgctgaa cagcgtgaac gttatttaca 5880
ggccagcgcc gattgccaaa gtcccgcccc tgccagcggc gttgtttatg aacttttgt 5940 cgccggcaaa ggcaaaacct ttacagcgaa accgaaaccg gacgcagaaa ttgcctcgct 6000
gttagcgaaa cgttcctctt gcggtaaaga cactctctat ttctctctgc gctatttgcc 6060
cgtcgcgcac ggcattctcg agtattaa 6088

<210> SEQ ID NO 44
<211> LENGTH: 885
<212> TYPE: DNA
<213> ORGANISM: Escherichia coli

<400> SEQUENCE: 44
atgaaaaaaa cattactggc agccggtgcg gtactggcgc tctcttcgtc ttttactgtc 60
aacgcagctg aaaacgacaa accgcagtat ctttccgact ggtggcacca gagcgttaac 120
gttgtcggaa gctatcacac ccgtttcgga ccgcagatcc gcaacgatac ctaccttgag 180
tacgaagcat tcgctaaaaa agactggttc gacttctatg gttatgcgga tgcgccggta 240
ttcttcggcg gtaactccga tgctaaaggt atctggaacc acggttctcc gctgtttatg 300
gaaatcgaac cacgtttctc catcgacaag ctgaccaata ctgaccttag cttcggtccg 360

```
ttcaaagagt ggtacttcgc gaacaactac atttacgaca tgggtcgtaa taaagatggt    420

cgccagagca cctggtacat gggtctgggt accgatatcg acactggcct gccgatgagc    480

ctgtccatga acgtctatgc gaaataccag tggcagaact atggcgcagc gaacgaaaac    540

gagtgggacg gttaccgttt caaaattaaa tactttgtgc cgattaccga tctgtggggc    600

ggtcagctga gctacatcgg cttcaccaac ttcgactggg gttccgattt aggggatgac    660

agcggtaacg caatcaacgg tattaagacc cgtactaata actctatcgc ttccagccat    720

attctggctc tgaactacga tcactggcac tactctgtcg tagctcgtta ctggcacgac    780

ggtggtcagt ggaacgacga tgcagaactg aacttcggca acggcaactt caacgttcgc    840

tctaccggct ggggtggtta cctggtagta ggttacaact tctga                    885
```

```
<210> SEQ ID NO 45
<211> LENGTH: 294
<212> TYPE: PRT
<213> ORGANISM: Escherichia coli

<400> SEQUENCE: 45

Met Lys Lys Thr Leu Leu Ala Ala Gly Ala Val Leu Ala Leu Ser Ser
1               5                   10                  15

Ser Phe Thr Val Asn Ala Ala Glu Asn Asp Lys Pro Gln Tyr Leu Ser
            20                  25                  30

Asp Trp Trp His Gln Ser Val Asn Val Val Gly Ser Tyr His Thr Arg
        35                  40                  45

Phe Gly Pro Gln Ile Arg Asn Asp Thr Tyr Leu Glu Tyr Glu Ala Phe
    50                  55                  60

Ala Lys Lys Asp Trp Phe Asp Phe Tyr Gly Tyr Ala Asp Ala Pro Val
65                  70                  75                  80

Phe Phe Gly Gly Asn Ser Asp Ala Lys Gly Ile Trp Asn His Gly Ser
                85                  90                  95

Pro Leu Phe Met Glu Ile Glu Pro Arg Phe Ser Ile Asp Lys Leu Thr
            100                 105                 110

Asn Thr Asp Leu Ser Phe Gly Pro Phe Lys Glu Trp Tyr Phe Ala Asn
        115                 120                 125

Asn Tyr Ile Tyr Asp Met Gly Arg Asn Lys Asp Gly Arg Gln Ser Thr
    130                 135                 140

Trp Tyr Met Gly Leu Gly Thr Asp Ile Asp Thr Gly Leu Pro Met Ser
145                 150                 155                 160

Leu Ser Met Asn Val Tyr Ala Lys Tyr Gln Trp Gln Asn Tyr Gly Ala
                165                 170                 175

Ala Asn Glu Asn Glu Trp Asp Gly Tyr Arg Phe Lys Ile Lys Tyr Phe
            180                 185                 190

Val Pro Ile Thr Asp Leu Trp Gly Gly Gln Leu Ser Tyr Ile Gly Phe
        195                 200                 205

Thr Asn Phe Asp Trp Gly Ser Asp Leu Gly Asp Asp Ser Gly Asn Ala
    210                 215                 220

Ile Asn Gly Ile Lys Thr Arg Thr Asn Asn Ser Ile Ala Ser Ser His
225                 230                 235                 240

Ile Leu Ala Leu Asn Tyr Asp His Trp His Tyr Ser Val Val Ala Arg
                245                 250                 255

Tyr Trp His Asp Gly Gly Gln Trp Asn Asp Asp Ala Glu Leu Asn Phe
            260                 265                 270

Gly Asn Gly Asn Phe Asn Val Arg Ser Thr Gly Trp Gly Gly Tyr Leu
```

```
        275                 280                 285

Val Val Gly Tyr Asn Phe
    290


<210> SEQ ID NO 46
<211> LENGTH: 2244
<212> TYPE: DNA
<213> ORGANISM: Escherichia coli

<400> SEQUENCE: 46

atggcgcgtt ccaaaactgc tcagccaaaa cactcactgc gtaaaatcgc agttgtagta      60

gccacagcgg ttagcggcat gtctgtttat gcacaggcag cggttgaacc gaaagaagac     120

actatcaccg ttaccgctgc acctgcgccg caagaaagcg catgggggcc tgctgcaact     180

attgcggcgc gacagtctgc taccggcact aaaaccgata cgccgattca aaaagtgcca     240

cagtctattt ctgttgtgac cgccgaagag atggcgctgc atcagccgaa gtcggtaaaa     300

gaagcgctta gctacacgcc gggtgtctct gttggtacgc gtggcgcatc caacacctat     360

gaccacctga tcattcgcgg ctttgcggca gaaggccaaa gccagaataa ctatctgaat     420

ggcctgaagt tgcagggcaa cttctataac gatgcggtca ttgacccgta tatgctggaa     480

cgcgctgaaa ttatgcgtgg cccggtttcc gtgctttacg gtaaaagcag tcctggcggc     540

ctgttgaata tggtcagcaa gcgtccgacc accgaaccgc tgaaagaagt tcagtttaaa     600

gccggtactg acagcctgtt ccagactggt tttgacttta gcgattcgtt ggatgatgac     660

ggtgtttact cttatcgcct gaccggtctt gcgcgttctg ccaatgccca gcagaaaggg     720

tcagaagagc agcgttatgc tattgcaccg gcgttcacct ggcgtccgga tgataaaacc     780

aattttacct tcctttctta cttccagaac gagccggaaa ccggttatta cggctggttg     840

ccgaaagagg gaaccgttga gccgctgccg aacggtaagc gtctgccgac agactttaat     900

gaaggggcga agaacaacac ctattctcgt aatgagaaga tggtcggcta cagcttcgat     960

cacgaattta acgacacctt tactgtgcgt cagaacctgc gctttgctga aaacaaaacc    1020

tcgcaaaaca gcgtttatgg ttacggcgtc tgctccgatc cggcgaatgc ttacagcaaa    1080

cagtgtgcgg cattagcgcc agcggataaa ggccattatc tggcacgtaa atacgtcgtt    1140

gatgatgaga agctgcaaaa cttctccgtt gatacccagt tgcagagcaa gtttgccact    1200

ggcgatatcg accacaccct gctgaccggt gtcgacttta tgcgtatgcg taatgacatc    1260

aacgcctggt ttggttacga cgactctgtg ccactgctca atctgtacaa tccggtgaat    1320

accgatttcg acttcaatgc caaagatccg gcaaactccg gcccttaccg cattctgaat    1380

aaacagaaac aaacgggcgt ttatgttcag gatcaggcgc agtgggataa agtgctggtc    1440

accctaggcg gtcgttatga ctgggcagat caagaatctc ttaaccgcgt tgccgggacg    1500

accgataaac gtgatgacaa acagtttacc tggcgtggtg gtgttaacta cctgtttgat    1560

aatggtgtaa caccttactt cagctatagc gaatcgtttg aaccttcttc gcaagttggg    1620

aaggatggta atattttcgc accgtctaaa ggtaagcagt atgaagtcgg cgtgaaatat    1680

gtaccggaag atcgtccgat tgtagttact ggtgccgtgt ataatctcac taaaaccaac    1740

aacctgatgg cggaccctga gggttccttc ttctcggttg aaggtggcga gatccgcgca    1800

cgtggcgtag aaatcgaagc gaaagcggcg ctgtcggcga gtgttaacgt agtcggttct    1860

tatacttaca ccgatgcgga atacaccacc gatactacct ataaaggcaa tacgcctgca    1920

caggtgccaa aacacatggc ttcgttgtgg gctgactaca ccttctttga cggtccgctt    1980
```

```
tcaggtctga cgctgggcac cggtggtcgt tatactggct ccagttatgg tgatccggct   2040

aactccttta aagtgggaag ttatacggtc gtggatgcgt tagtacgtta tgatctggcg   2100

cgagtcggca tggctggctc caacgtggcg ctgcatgtta acaacctgtt cgatcgtgaa   2160

tacgtcgcca gctgctttaa cacttatggc tgcttctggg gcgcagaacg tcaggtcgtt   2220

gcaaccgcaa ccttccgttt ctaa                                           2244


<210> SEQ ID NO 47
<211> LENGTH: 747
<212> TYPE: PRT
<213> ORGANISM: Escherichia coli

<400> SEQUENCE: 47

Met Ala Arg Ser Lys Thr Ala Gln Pro Lys His Ser Leu Arg Lys Ile
1               5                   10                  15

Ala Val Val Val Ala Thr Ala Val Ser Gly Met Ser Val Tyr Ala Gln
            20                  25                  30

Ala Ala Val Glu Pro Lys Glu Asp Thr Ile Thr Val Thr Ala Ala Pro
        35                  40                  45

Ala Pro Gln Glu Ser Ala Trp Gly Pro Ala Ala Thr Ile Ala Ala Arg
    50                  55                  60

Gln Ser Ala Thr Gly Thr Lys Thr Asp Thr Pro Ile Gln Lys Val Pro
65                  70                  75                  80

Gln Ser Ile Ser Val Val Thr Ala Glu Glu Met Ala Leu His Gln Pro
                85                  90                  95

Lys Ser Val Lys Glu Ala Leu Ser Tyr Thr Pro Gly Val Ser Val Gly
            100                 105                 110

Thr Arg Gly Ala Ser Asn Thr Tyr Asp His Leu Ile Ile Arg Gly Phe
        115                 120                 125

Ala Ala Glu Gly Gln Ser Gln Asn Asn Tyr Leu Asn Gly Leu Lys Leu
    130                 135                 140

Gln Gly Asn Phe Tyr Asn Asp Ala Val Ile Asp Pro Tyr Met Leu Glu
145                 150                 155                 160

Arg Ala Glu Ile Met Arg Gly Pro Val Ser Val Leu Tyr Gly Lys Ser
                165                 170                 175

Ser Pro Gly Gly Leu Leu Asn Met Val Ser Lys Arg Pro Thr Thr Glu
            180                 185                 190

Pro Leu Lys Glu Val Gln Phe Lys Ala Gly Thr Asp Ser Leu Phe Gln
        195                 200                 205

Thr Gly Phe Asp Phe Ser Asp Ser Leu Asp Asp Asp Gly Val Tyr Ser
    210                 215                 220

Tyr Arg Leu Thr Gly Leu Ala Arg Ser Ala Asn Ala Gln Gln Lys Gly
225                 230                 235                 240

Ser Glu Glu Gln Arg Tyr Ala Ile Ala Pro Ala Phe Thr Trp Arg Pro
                245                 250                 255

Asp Asp Lys Thr Asn Phe Thr Phe Leu Ser Tyr Phe Gln Asn Glu Pro
            260                 265                 270

Glu Thr Gly Tyr Tyr Gly Trp Leu Pro Lys Glu Gly Thr Val Glu Pro
        275                 280                 285

Leu Pro Asn Gly Lys Arg Leu Pro Thr Asp Phe Asn Glu Gly Ala Lys
    290                 295                 300

Asn Asn Thr Tyr Ser Arg Asn Glu Lys Met Val Gly Tyr Ser Phe Asp
305                 310                 315                 320

His Glu Phe Asn Asp Thr Phe Thr Val Arg Gln Asn Leu Arg Phe Ala
```

```
                325                 330                 335

Glu Asn Lys Thr Ser Gln Asn Ser Val Tyr Gly Tyr Gly Val Cys Ser
            340                 345                 350

Asp Pro Ala Asn Ala Tyr Ser Lys Gln Cys Ala Ala Leu Ala Pro Ala
        355                 360                 365

Asp Lys Gly His Tyr Leu Ala Arg Lys Tyr Val Val Asp Asp Glu Lys
    370                 375                 380

Leu Gln Asn Phe Ser Val Asp Thr Gln Leu Gln Ser Lys Phe Ala Thr
385                 390                 395                 400

Gly Asp Ile Asp His Thr Leu Leu Thr Gly Val Asp Phe Met Arg Met
                405                 410                 415

Arg Asn Asp Ile Asn Ala Trp Phe Gly Tyr Asp Asp Ser Val Pro Leu
            420                 425                 430

Leu Asn Leu Tyr Asn Pro Val Asn Thr Asp Phe Asp Phe Asn Ala Lys
        435                 440                 445

Asp Pro Ala Asn Ser Gly Pro Tyr Arg Ile Leu Asn Lys Gln Lys Gln
    450                 455                 460

Thr Gly Val Tyr Val Gln Asp Gln Ala Gln Trp Asp Lys Val Leu Val
465                 470                 475                 480

Thr Leu Gly Gly Arg Tyr Asp Trp Ala Asp Gln Glu Ser Leu Asn Arg
                485                 490                 495

Val Ala Gly Thr Thr Asp Lys Arg Asp Asp Lys Gln Phe Thr Trp Arg
            500                 505                 510

Gly Gly Val Asn Tyr Leu Phe Asp Asn Gly Val Thr Pro Tyr Phe Ser
        515                 520                 525

Tyr Ser Glu Ser Phe Glu Pro Ser Ser Gln Val Gly Lys Asp Gly Asn
    530                 535                 540

Ile Phe Ala Pro Ser Lys Gly Lys Gln Tyr Glu Val Gly Val Lys Tyr
545                 550                 555                 560

Val Pro Glu Asp Arg Pro Ile Val Val Thr Gly Ala Val Tyr Asn Leu
                565                 570                 575

Thr Lys Thr Asn Asn Leu Met Ala Asp Pro Glu Gly Ser Phe Phe Ser
            580                 585                 590

Val Glu Gly Gly Glu Ile Arg Ala Arg Gly Val Glu Ile Glu Ala Lys
        595                 600                 605

Ala Ala Leu Ser Ala Ser Val Asn Val Val Gly Ser Tyr Thr Tyr Thr
    610                 615                 620

Asp Ala Glu Tyr Thr Thr Asp Thr Thr Tyr Lys Gly Asn Thr Pro Ala
625                 630                 635                 640

Gln Val Pro Lys His Met Ala Ser Leu Trp Ala Asp Tyr Thr Phe Phe
                645                 650                 655

Asp Gly Pro Leu Ser Gly Leu Thr Leu Gly Thr Gly Gly Arg Tyr Thr
            660                 665                 670

Gly Ser Ser Tyr Gly Asp Pro Ala Asn Ser Phe Lys Val Gly Ser Tyr
        675                 680                 685

Thr Val Val Asp Ala Leu Val Arg Tyr Asp Leu Ala Arg Val Gly Met
    690                 695                 700

Ala Gly Ser Asn Val Ala Leu His Val Asn Asn Leu Phe Asp Arg Glu
705                 710                 715                 720

Tyr Val Ala Ser Cys Phe Asn Thr Tyr Gly Cys Phe Trp Gly Ala Glu
                725                 730                 735

Arg Gln Val Val Ala Thr Ala Thr Phe Arg Phe
            740                 745
```

<210> SEQ ID NO 48
<211> LENGTH: 1341
<212> TYPE: DNA
<213> ORGANISM: Escherichia coli

<400> SEQUENCE: 48

```
atgatgatta ctctgcgcaa acttcctctg gcggttgccg tcgcagcggg cgtaatgtct     60
gctcaggcaa tggctgttga tttccacggc tatgcacgtt ccggtattgg ttggacaggt    120
agcggcggtg aacaacagtg tttccagact accggtgctc aaagtaaata ccgtcttggc    180
aacgaatgtg aaacttatgc tgaattaaaa ttgggtcagg aagtgtggaa agagggcgat    240
aagagcttct atttcgacac taacgtggcc tattccgtcg cacaacagaa tgactgggaa    300
gctaccgatc cggccttccg tgaagcaaac gtgcagggta aaaacctgat cgaatggctg    360
ccaggctcca ccatctgggc aggtaagcgc ttctaccaac gtcatgacgt tcatatgatc    420
gacttctact actgggatat ttctggtcct ggtgccggtc tggaaaacat cgatgttggc    480
ttcggtaaac tctctctggc agcaacccgc tcctctgaag ctggtggttc ttcctctttc    540
gccagcaaca atatttatga ctataccaac gaaaccgcga acgacgtttt cgatgtgcgt    600
ttagcgcaga tggaaatcaa cccgggcggc acattagaac tgggtgtcga ctacggtcgt    660
gccaacttgc gtgataacta tcgtctggtt gatggcgcat cgaaagacgg ctggttattc    720
actgctgaac atactcagag tgtcctgaag ggctttaaca agtttgttgt tcagtacgct    780
actgactcga tgacctcgca gggtaaaggg ctgtcgcagg gttctggcgt tgcatttgat    840
aacgaaaaat ttgcctacaa tatcaacaac aacggtcaca tgctgcgtat cctcgaccac    900
ggtgcgatct ccatgggcga caactgggac atgatgtacg tgggtatgta ccaggatatc    960
aactgggata acgacaacgg caccaagtgg tggaccgtcg gtattcgccc gatgtacaag   1020
tggacgccaa tcatgagcac cgtgatggaa atcggctacg acaacgtcga atcccagcgc   1080
accggcgaca agaacaatca gtacaaaatt accctcgcac aacaatggca ggctggcgac   1140
agcatctggt cacgcccggc tattcgtgtc ttcgcaacct acgccaagtg ggatgagaaa   1200
tggggttacg actacaccgg taacgctgat aacaacgcga acttcggcaa agccgttcct   1260
gctgatttca acggcggcag cttcggtcgt ggcgacagcg acgagtggac cttcggtgcc   1320
cagatggaaa tctggtggta a                                             1341
```

<210> SEQ ID NO 49
<211> LENGTH: 446
<212> TYPE: PRT
<213> ORGANISM: Escherichia coli

<400> SEQUENCE: 49

```
Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
            20                  25                  30

Arg Ser Gly Ile Gly Trp Thr Gly Ser Gly Gly Glu Gln Gln Cys Phe
        35                  40                  45

Gln Thr Thr Gly Ala Gln Ser Lys Tyr Arg Leu Gly Asn Glu Cys Glu
    50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Ala Gln Gln
```

```
                85                  90                  95

Asn Asp Trp Glu Ala Thr Asp Pro Ala Phe Arg Glu Ala Asn Val Gln
            100                 105                 110

Gly Lys Asn Leu Ile Glu Trp Leu Pro Gly Ser Thr Ile Trp Ala Gly
        115                 120                 125

Lys Arg Phe Tyr Gln Arg His Asp Val His Met Ile Asp Phe Tyr Tyr
    130                 135                 140

Trp Asp Ile Ser Gly Pro Gly Ala Gly Leu Glu Asn Ile Asp Val Gly
145                 150                 155                 160

Phe Gly Lys Leu Ser Leu Ala Ala Thr Arg Ser Ser Glu Ala Gly Gly
                165                 170                 175

Ser Ser Ser Phe Ala Ser Asn Asn Ile Tyr Asp Tyr Thr Asn Glu Thr
            180                 185                 190

Ala Asn Asp Val Phe Asp Val Arg Leu Ala Gln Met Glu Ile Asn Pro
        195                 200                 205

Gly Gly Thr Leu Glu Leu Gly Val Asp Tyr Gly Arg Ala Asn Leu Arg
    210                 215                 220

Asp Asn Tyr Arg Leu Val Asp Gly Ala Ser Lys Asp Gly Trp Leu Phe
225                 230                 235                 240

Thr Ala Glu His Thr Gln Ser Val Leu Lys Gly Phe Asn Lys Phe Val
                245                 250                 255

Val Gln Tyr Ala Thr Asp Ser Met Thr Ser Gln Gly Lys Gly Leu Ser
            260                 265                 270

Gln Gly Ser Gly Val Ala Phe Asp Asn Glu Lys Phe Ala Tyr Asn Ile
        275                 280                 285

Asn Asn Asn Gly His Met Leu Arg Ile Leu Asp His Gly Ala Ile Ser
    290                 295                 300

Met Gly Asp Asn Trp Asp Met Met Tyr Val Gly Met Tyr Gln Asp Ile
305                 310                 315                 320

Asn Trp Asp Asn Asp Asn Gly Thr Lys Trp Trp Thr Val Gly Ile Arg
                325                 330                 335

Pro Met Tyr Lys Trp Thr Pro Ile Met Ser Thr Val Met Glu Ile Gly
            340                 345                 350

Tyr Asp Asn Val Glu Ser Gln Arg Thr Gly Asp Lys Asn Asn Gln Tyr
        355                 360                 365

Lys Ile Thr Leu Ala Gln Gln Trp Gln Ala Gly Asp Ser Ile Trp Ser
    370                 375                 380

Arg Pro Ala Ile Arg Val Phe Ala Thr Tyr Ala Lys Trp Asp Glu Lys
385                 390                 395                 400

Trp Gly Tyr Asp Tyr Thr Gly Asn Ala Asp Asn Asn Ala Asn Phe Gly
                405                 410                 415

Lys Ala Val Pro Ala Asp Phe Asn Gly Gly Ser Phe Gly Arg Gly Asp
            420                 425                 430

Ser Asp Glu Trp Thr Phe Gly Ala Gln Met Glu Ile Trp Trp
        435                 440                 445
```

<210> SEQ ID NO 50
<211> LENGTH: 1845
<212> TYPE: DNA
<213> ORGANISM: Escherichia coli

<400> SEQUENCE: 50

```
atgattaaaa aagcttcgct gctgacggcg tgttccgtca cggcattttc cgcttgggca      60

caggatacca gcccggatac tctcgtcgtt actgctaacc gttttgaaca gccgcgcagc     120
```

```
actgtgcttg caccaaccac cgttgtgacc cgtcaggata tcgaccgctg gcagtcgacc    180

tcggtcaatg atgtgctgcg ccgtcttccg ggcgtcgata tcacccaaaa cggcggttca    240

ggtcagctct catctatttt tattcgcggt acaaatgcca gtcatgtgtt ggtgttaatt    300

gatggcgtac gcctgaatct ggcgggggtg agtggttctg ccgaccttag ccagttccct    360

attgcgcttg tccagcgtgt tgaatatatc cgtgggccgc gctccgctgt ttatggttcc    420

gatgcaatag gcggggtggt gaatatcatc acgacgcgcg atgaacccgg aacggaaatt    480

tcagcagggt ggggaagcaa tagttatcag aactatgatg tctctacgca gcaacaactg    540

gggggataaga cacgggtaac gctgttgggc gattatgccc atactcatgg ttatgatgtt    600

gttgcctatg gtaataccgg aacgcaagcg cagacagata acgatggttt tttaagtaaa    660

acgctttatg gcgcgctgga gcataacttt actgatgcct ggagcggctt tgtgcgcggc    720

tatggctatg ataaccgtac caattatgac gcgtattatt ctcccggttc accgttgctc    780

gatacccgta aactctatag ccaaagttgg gacgccgggc tgcgctataa cggcgaactg    840

attaaatcac aactcattac cagctatagc catagcaaag attacaacta cgatccccat    900

tatggtcgtt atgattcgtc ggcgacgctc gatgagatga agcaatacac cgtccagtgg    960

gcaaacaatg tcatcgttgg tcacggtagt attggtgcgg gtgtcgactg gcagaaacag   1020

actacgacgc cgggtacagg ttatgttgag gatggatatg atcaacgtaa taccggcatc   1080

tatctgaccg ggctgcaaca agtcggcgat tttacctttg aaggcgcagc acgcagtgac   1140

gataactcac agtttggtcg tcatggaacc tggcaaacca gcgccggttg ggaattcatc   1200

gaaggttatc gcttcattgc ttcctacggg acatcttata aggcaccaaa tctggggcaa   1260

ctgtatggct tctacggaaa tccgaatctg gacccggaga aaagcaaaca gtgggaaggc   1320

gcgtttgaag gcttaaccgc tggggtgaac tggcgtattt ccggatatcg taacgatgtc   1380

agtgacttga tcgattatga tgatcacacc ctgaaatatt acaacgaagg gaaagcgcgg   1440

attaagggcg tcgaggcgac cgccaatttt gataccggac cactgacgca tactgtgagt   1500

tatgattatg tcgatgcgcg caatgcgatt accgacacgc cgttgttacg ccgtgctaaa   1560

cagcaggtga aataccagct cgactggcag ttgtatgact tcgactgggg tattacttat   1620

cagtatttag gcactcgcta tgataaggat tactcatctt atccttatca aaccgttaaa   1680

atgggcggtg tgagcttgtg ggatcttgcg gttgcgtatc cggtcacctc tcacctgaca   1740

gttcgtggta aaatagccaa cctgttcgac aaagattatg agacagtcta tggctaccaa   1800

actgcaggac gggaatacac cttgtctggc agctacacct tctga                   1845
```

<210> SEQ ID NO 51
<211> LENGTH: 614
<212> TYPE: PRT
<213> ORGANISM: Escherichia coli

<400> SEQUENCE: 51

```
Met Ile Lys Lys Ala Ser Leu Leu Thr Ala Cys Ser Val Thr Ala Phe
1               5                   10                  15

Ser Ala Trp Ala Gln Asp Thr Ser Pro Asp Thr Leu Val Val Thr Ala
            20                  25                  30

Asn Arg Phe Glu Gln Pro Arg Ser Thr Val Leu Ala Pro Thr Thr Val
        35                  40                  45

Val Thr Arg Gln Asp Ile Asp Arg Trp Gln Ser Thr Ser Val Asn Asp
    50                  55                  60
```

```
Val Leu Arg Arg Leu Pro Gly Val Asp Ile Thr Gln Asn Gly Gly Ser
65                  70                  75                  80

Gly Gln Leu Ser Ser Ile Phe Ile Arg Gly Thr Asn Ala Ser His Val
                85                  90                  95

Leu Val Leu Ile Asp Gly Val Arg Leu Asn Leu Ala Gly Val Ser Gly
            100                 105                 110

Ser Ala Asp Leu Ser Gln Phe Pro Ile Ala Leu Val Gln Arg Val Glu
        115                 120                 125

Tyr Ile Arg Gly Pro Arg Ser Ala Val Tyr Gly Ser Asp Ala Ile Gly
    130                 135                 140

Gly Val Val Asn Ile Ile Thr Thr Arg Asp Glu Pro Gly Thr Glu Ile
145                 150                 155                 160

Ser Ala Gly Trp Gly Ser Asn Ser Tyr Gln Asn Tyr Asp Val Ser Thr
                165                 170                 175

Gln Gln Gln Leu Gly Asp Lys Thr Arg Val Thr Leu Leu Gly Asp Tyr
            180                 185                 190

Ala His Thr His Gly Tyr Asp Val Val Ala Tyr Gly Asn Thr Gly Thr
        195                 200                 205

Gln Ala Gln Thr Asp Asn Asp Gly Phe Leu Ser Lys Thr Leu Tyr Gly
    210                 215                 220

Ala Leu Glu His Asn Phe Thr Asp Ala Trp Ser Gly Phe Val Arg Gly
225                 230                 235                 240

Tyr Gly Tyr Asp Asn Arg Thr Asn Tyr Asp Ala Tyr Tyr Ser Pro Gly
                245                 250                 255

Ser Pro Leu Leu Asp Thr Arg Lys Leu Tyr Ser Gln Ser Trp Asp Ala
            260                 265                 270

Gly Leu Arg Tyr Asn Gly Glu Leu Ile Lys Ser Gln Leu Ile Thr Ser
        275                 280                 285

Tyr Ser His Ser Lys Asp Tyr Asn Tyr Asp Pro His Tyr Gly Arg Tyr
    290                 295                 300

Asp Ser Ser Ala Thr Leu Asp Glu Met Lys Gln Tyr Thr Val Gln Trp
305                 310                 315                 320

Ala Asn Asn Val Ile Val Gly His Gly Ser Ile Gly Ala Gly Val Asp
                325                 330                 335

Trp Gln Lys Gln Thr Thr Thr Pro Gly Thr Gly Tyr Val Glu Asp Gly
            340                 345                 350

Tyr Asp Gln Arg Asn Thr Gly Ile Tyr Leu Thr Gly Leu Gln Gln Val
        355                 360                 365

Gly Asp Phe Thr Phe Glu Gly Ala Ala Arg Ser Asp Asp Asn Ser Gln
    370                 375                 380

Phe Gly Arg His Gly Thr Trp Gln Thr Ser Ala Gly Trp Glu Phe Ile
385                 390                 395                 400

Glu Gly Tyr Arg Phe Ile Ala Ser Tyr Gly Thr Ser Tyr Lys Ala Pro
                405                 410                 415

Asn Leu Gly Gln Leu Tyr Gly Phe Tyr Gly Asn Pro Asn Leu Asp Pro
            420                 425                 430

Glu Lys Ser Lys Gln Trp Glu Gly Ala Phe Glu Gly Leu Thr Ala Gly
        435                 440                 445

Val Asn Trp Arg Ile Ser Gly Tyr Arg Asn Asp Val Ser Asp Leu Ile
    450                 455                 460

Asp Tyr Asp Asp His Thr Leu Lys Tyr Tyr Asn Glu Gly Lys Ala Arg
465                 470                 475                 480

Ile Lys Gly Val Glu Ala Thr Ala Asn Phe Asp Thr Gly Pro Leu Thr
```

-continued

```
                485                 490                 495

His Thr Val Ser Tyr Asp Tyr Val Asp Ala Arg Asn Ala Ile Thr Asp
            500                 505                 510

Thr Pro Leu Leu Arg Arg Ala Lys Gln Gln Val Lys Tyr Gln Leu Asp
        515                 520                 525

Trp Gln Leu Tyr Asp Phe Asp Trp Gly Ile Thr Tyr Gln Tyr Leu Gly
    530                 535                 540

Thr Arg Tyr Asp Lys Asp Tyr Ser Ser Tyr Pro Tyr Gln Thr Val Lys
545                 550                 555                 560

Met Gly Gly Val Ser Leu Trp Asp Leu Ala Val Ala Tyr Pro Val Thr
                565                 570                 575

Ser His Leu Thr Val Arg Gly Lys Ile Ala Asn Leu Phe Asp Lys Asp
            580                 585                 590

Tyr Glu Thr Val Tyr Gly Tyr Gln Thr Ala Gly Arg Glu Tyr Thr Leu
        595                 600                 605

Ser Gly Ser Tyr Thr Phe
    610
```

MICROORGANISMS PRODUCING L-AMINO ACIDS AND PROCESS FOR PRODUCING L-AMINO ACIDS USING THE SAME

TECHNICAL FIELD

The present invention relates to a recombinant microorganism producing an L-amino acid and a method of producing an L-amino acid using the recombinant microorganism.

BACKGROUND ART

Various fermentation processes using microorganisms for mass production of useful metabolites, e.g., amino acids, have been used, and furthermore, a variety of techniques including strain development, establishment of fermentation conditions, or the like, have been developed for successful fermentation using the microorganisms. In particular, for the development of a host strain for mass production of useful metabolites, many attempts have been made to induce over-expression or low-expression of a specific gene.

However, in fermentative production using bacteria, the production of useful metabolites may be reduced due to contamination of phages. The contamination of phages is caused mainly due to phage receptors, which are proteins, lipid polysaccharides, or the like, that are capable of attaching phages to a bacterial surface. In the case of *Escherichia coli* (*E. coli*), *E. coli* is attacked by a variety of phages, and accordingly, the study of receptors for each of the phages has been relatively successful. However, the study of the relationship between the phage receptors and the production of L-amino acids has not been sufficiently carried out yet.

In this regard, the inventors of the present invention select genes that are well-known phage receptors, and then, inactivate each of the genes, to reduce the risk of reduction of the L-amino acid production, the risk being considered as a vulnerability of *E. coli*. Afterwards, the influence on the L-amino acid production is confirmed, and such selection and inactivation of the genes are applied to L-amino acid-producing strains, thereby completing the present invention.

DISCLOSURE OF INVENTION

Technical Problem

The present invention provides a recombinant microorganism having L-amino acid producibility and an inactivated phage receptor.

The present invention provides a method of producing an L-amino acid using the microorganism.

Solution to Problem

In one aspect, the present invention provides a recombinant microorganism producing L-amino acid in which at least one of NfrA and NfrB are inactivated.

The term "NrfA" as used herein refers to a protein forming a receptor for bacteriophage N4, and may be a membrane protein of bacteria. For example, NrfA may be a subunit of an outer membrane protein. The NfrA may include, for example, an amino acid sequence of SEQ ID NO: 40. The NfrA may include, for example, an amino acid sequence of SEQ ID NO: 40, or an amino acid sequence having about 80% or more, 85% or more, 90% or more, or 95% or more sequence identity with the amino acid sequence of SEQ ID NO: 40. A sequence of a gene encoding the NfrA may include a polynucleotide sequence encoding the amino acid sequence of SEQ ID NO: 40. The sequence of the gene encoding the NfrA may include, for example, a sequence of an nfrA gene (NCBI Gene ID: 12930896). For example, the sequence of the gene encoding the NfrA may include a polynucleotide sequence of SEQ ID NO: 39, or a polynucleotide sequence having about 80% or more, 85% or more, 90% or more, or 95% or more sequence identity with the polynucleotide sequence of SEQ ID NO: 39.

The term "NfrB" as used herein refers to a protein forming a receptor for bacteriophage N4, and may be a membrane protein of bacteria. For example, NfrB may be a subunit of an inner membrane protein. The NfrB may include, for example, an amino acid sequence of SEQ ID NO: 42. The NfrB may include, for example, am amino acid sequence of SEQ ID NO: 42, or an amino acid sequence having about 80% or more, 85% or more, 90% or more, or 95% or more sequence identity with the amino acid sequence of SEQ ID NO: 42. A sequence of a gene encoding the NfrB may include a polynucleotide sequence encoding the amino acid sequence of SEQ ID NO: 42. The sequence of the gene encoding the NfrB may include, for example, a sequence of an nfrB gene (NCBI Gene ID: 12933943). For example, the sequence of the gene encoding the NfrB protein may include a polynucleotide sequence of SEQ ID NO: 41, or a polynucleotide sequence having about 80% or more, 85% or more, 90% or more, or 95% or more sequence identity with the polynucleotide sequence of SEQ ID NO: 41.

In addition, in the recombinant microorganism producing an L-amino acid, at least one of Tsx and FhuA may be further inactivated.

The term "Tsx" as used herein refers to a protein forming a nucleoside channel, i.e., a channel specific to a nucleoside, and may be a component forming a receptor for phage T6 and colicin K. The Tsx may include, for example, an amino acid sequence of SEQ ID NO: 45, or an amino acid sequence having about 80% or more, 85% or more, 90% or more, or 95% or more sequence identity with the amino acid sequence of SEQ ID NO: 45. A sequence of a gene encoding gene the Tsx may include a polynucleotide sequence encoding the amino acid sequence of SEQ ID NO: 45. The sequence of the gene encoding the Tsx may include, for example, a sequence of a tsx gene (NCBI Gene ID: 12934188). For example, the sequence of the gene encoding the Tsx may include a polynucleotide sequence of SEQ ID NO: 44, or a polynucleotide sequence having about 80% or more, 85% or more, 90% or more, or 95% or more sequence identity with the polynucleotide sequence of SEQ ID NO: 44.

The term "FhuA" as used herein refers to a multifunctional protein in an outer membrane of bacteria that transports ($Fe^{3+}$) ferrichrome or antibiotics, such as albomycin and rifamycin, and may be a receptor for phages T1, T5, and phi80. The FhuA may include, for example, an amino acid sequence of SEQ ID NO: 47, or an amino acid sequence having about 80% or more, 85% or more, 90% or more, or 95% or more sequence identity with the amino acid sequence of SEQ ID NO: 47. A sequence of a gene encoding the FhuA may include a polynucleotide sequence encoding the amino acid sequence of SEQ ID NO: 47. The sequence of the gene encoding the FhuA protein may include, for example, a sequence of an fhuA gene (NCBI Gene ID: 12930751). For example, the sequence of the gene encoding the FhuA may include a polynucleotide sequence of SEQ ID NO: 47, or a polynucleotide sequence having about 80% or more, 85% or more, 90% or more, or 95% or more sequence identity with the polynucleotide sequence of SEQ ID NO: 47.

The term "identity" as used herein refers to sameness between two amino acid sequences, which may be determined by a method that is well known in the art, e.g., the BLAST 2.0 algorithm that defines parameters, such as a score, an identity, and a similarity between two amino acid sequences.

The term "recombinant microorganism" as used herein refers to a microorganism that is genetically modified. The recombinant microorganism may be a microorganism that is genetically engineered, and for example, an exogenous nucleic acid may be introduced to a microorganism according to genetic engineering methods, or a sequence or location of an endogenous gene in a microorganism may be transformed.

The term "L-amino acid" as used herein refers to a basic structural unit of a protein constituting the body of an organism and having both an amino group and a carboxylic acid group that are attached to the same carbon atom. For example, the L-amino acid may be selected from the group consisting of L-leucine, L-phenylalanine, L-lysine, L-threonine, L-valine, L-isoleucine, L-tryptophan, and L-methionine. For example, the L-amino acid may be L-tryptophan or L-threonine.

The term "an enzyme or a protein is inactivated" or "innactivation of an enzyme or a protein" as used herein refers to a case where the above-described protein is not expressed at all in a microorganism, a case where the above-described protein is expressed, but does not have any activity, or a case where the above-described protein is expressed, but activity thereof is weak compared to the intrinsic activity. The term "intrinsic activity" as used herein refers to activity of a microorganism in a natural state, i.e. activity originally existing in a microorganism, or activity of a protein that has not been genetically modified.

The inactivation of the NfrA protein, the NfrB protein, the Tsx protein, and the FhuA protein may be caused by mutation, deletion, or disruption of genes that each encode the NfrA protein, the NfrB protein, the Tsx protein, and the FhuA protein. The term "mutation, deletion, or disruption of the genes" as used herein refers to a case where a part or all of the genes or regulatory factors on promoter or terminator regions of the genes are mutated, substituted, deleted, or inserted with at least one base, so that the genes are not expressed or the genes are expressed in a small amount, or the genes are expressed without showing enzymatic activity or with decreased enzymatic activity. The mutation, deletion, or disruption of the genes may be achieved by genetic manipulation, such as homologous recombination, mutagenesis, or molecular evolution. When a cell includes a plurality of the same genes or at least two homologous genes, one or more genes may be deleted or disrupted in the cell. In order to inactivate the genes provided in an embodiment of the present invention, methods of manufacturing a mutant using a lambda Red recombinase may be carried out.

The recombinant microorganism removes or reduces activity of each of the proteins provided herein or the proteins in combination. Accordingly, the recombinant microorganism may have enhanced producibility of the L-amino acid compared to the case where the activity of the proteins is not inactivated, and thus, the recombinant microorganism may be appropriately used for the purpose of producing the L-amino acid.

The recombinant microorganism may be a microorganism of the genus *Escherichia*, the genus *Enterbacter*, the genus *Erwinia*, the genus *Serratia*, the genus *Providencia*, the genus *Corynebacterium*, and the genus *Brevibacterium*. For example, the recombinant microorganism may be a microorganism of the genus *Escherichia*. The microorganism of the genus *Escherichia* may be *Escherichia coli* (*E. coli*), e.g., KCCM11501P. The KCCM11501P is a KCCM10910PΔnfrAB strain prepared by using a threonine-producing strain (KCCM10910P) as a mother strain and performing deletion of both nfrA and nfrB genes. Here, sugar consumption capacity in the *E. coli* KCCM11501P is found to be higher than that in the mother strain (KCCM10910P). The KCCM11501P was named '*E. coli* CA03-8253P', and then, was deposited at the Korean Culture Center of Microorganisms (hereinafter, referred to as 'KCCM') on Dec. 13, 2013 under the Budapest Treaty.

According to another aspect of the present invention, a method of producing the L-amino acid is disclosed, the method including: culturing the recombinant microorganism producing the L-amino acid; and collecting the L-amino acid from the culture product.

The recombinant microorganism producing the L-amino acid is defined the same as described above.

The L-amino acid may be selected from the group consisting of L-leucine, L-phenylalanine, L-lysine, L-threonine, L-valine, L-isoleucine, L-tryptophan, and L-methionine. For example, the L-amino acid may be L-threonine or L-tryptophan. The culturing of the recombinant microorganism may be achieved in accordance with an appropriate culture medium and culture conditions that are well known in the art. In addition, one of ordinary skill in the art may appropriately adjust a culture medium and culture conditions according to the selected microorganism. The culture method may include a batch culture, a continuous culture, a fed-batch culture, or a combination thereof.

The culture medium may include a variety of carbon sources, nitrogen sources, and trace element ingredients.

The carbon sources may include, for example, carbohydrates, such as glucose, sucrose, lactose, fructose, maltose, starch, and cellulose; fats, such as soybean oil, sunflower oil, castor oil, and coconut oil; fatty acids, such as palmitic acid, stearic acid, and linoleic acid; alcohol, such as glycerol and ethanol; and organic acids, such as acetic acid, or a combination thereof. The culturing of the recombinant microorganism may be performed by using glucose as a carbon source. The nitrogen sources may include, for example, organic nitrogen sources, such as peptone, yeast extract, gravy, malt extract, corn steep liquor (CSL), and soybean flour; and inorganic nitrogen sources, such as urea, ammonium sulfate, ammonium chloride, ammonium phosphate, ammonium carbonate, and ammonium nitrate; or a combination thereof. The culture medium may include, as a phosphorus source, potassium dihydrogen phosphate or potassium hydrogen phosphate. In addition, the culture medium may include sodium-containing slats corresponding to the phosphorus source, and metal salts, such as magnesium sulfate or iron sulfate. In addition, the culture medium may include amino acids, vitamins, and appropriate precursors. The medium or individual ingredients of the medium may be added to the culture medium in a batch or continuous manner.

In addition, compounds, such as ammonium hydroxide, potassium hydroxide, ammonia, phosphoric acid, and sulfuric acid may be added to the culture medium during the culturing of the recombinant microorganism in an appropriate manner, so as to adjust pH of the culture medium. In addition, antifoaming agents, such as fatty acid polyglycol ester, may be used during the culturing of the recombinant microorganism, so as to suppress production of air bubbles. In order to maintain aerobic conditions of the culture medium, oxygen or oxygen-containing gas (e.g., air) may be injected into the culture medium. Here, a temperature of the culture medium may typically be in a range of about 20° C. to about 45° C. A period of the culturing of the recombinant microorganism may last until a desired amount of the L-amino acid is obtained, and for example, the culturing of the recombinant microorganism may last about 10 hours to about 160 hours.

The term "culture product" as used herein refers to a broth culture containing the recombinant microorganism, a culture supernatant from which a microbial cell is removed, or a diluted solution of the culture product. The culture medium may further include an ingredient for increasing the productivity of the L-amino acid. For example, the composition may further include carbon sources, nitrogen sources, or trace element ingredients.

The collecting of the L-amino acid from the culture product may be performed by appropriate culture methods known in the art, such as a batch culture, a continuous culture, or a fed-batch culture, so as to collect or recover the L-amino acid produced in the culture product.

Advantageous Effects of Invention

According to an aspect, a microorganism having removed or decreased activity of at least one protein selected from the group consisting of an NfrA protein, an NfrB protein, a Tsx protein, and an FhuA protein may be used to produce an L-amino acid.

According to another aspect, a method of producing an L-amino acid may be used to produce an L-amino acid in an efficient manner.

MODE FOR THE INVENTION

Hereinafter, the present invention will be described in further detail with reference to the following examples. These examples are for illustrative purposes only and are not intended to limit the scope of the present invention.

Example 1. Preparation of Threonine-Producing Strain Having Inactivated Phage Receptor by Using KCCM10910P In order to prepare a threonine-producing strain having an inactivated phage receptor, a KCCM10910P strain (Korean Patent No: 10-0966324) was used as a mother strain. Then, a cassette for inactivating a gene for each phage receptor was prepared, and then, was used to allow genetic transformation.

1-1. Preparation of Threonine-Producing Strain Having Inactivated nfrA Gene

In order to prepare a threonine-producing strain having an inactivated nfrA gene, a cassette for inactivating an nfrA gene was prepared. The cassette used a method of one step inactivation, which is a technique of constructing a mutant using lambda Red recombinase developed by Datsenko K A et al. (Proc Natl Acad Sci USA., (2000) 97:6640-6645). To confirm the insertion of the cassette into the gene, a chloramphenicol-resistant gene of pUCprmfmloxC was used as a marker (Korean Patent LaidOpen Publication NO: 2009-007554).

1.1 kb DNA fragment including a part of a sequence of the nfrA gene (SEQ ID NO: 39) and a part of a base sequence of the chloramphenicol-resistant gene of a pUCprmfmloxC was obtained by using a primer set of SEQ ID NOS: 2 and 3. Here, a polymerase chain reaction (hereinafter, referred to as "PCR") was performed by using a PCR premix kit (i.e., a product of BIONEER company, hereinafter, the same product was used) under the following conditions: 27 cycles of denaturation at 95° C. for 30 seconds, annealing at 56° C. for 30 seconds, and elongation at 72° C. for 1 minute. The PCR product was electrophoresed on a 0.8% agarose gel, and then, eluted. Afterwards, PCR was performed again by using the eluted product as a template and a primer set of SEQ ID NOS: 1 and 4 under the same conditions described above, resulting in a DNA fragment of about 1.2 kb. The DNA fragment was electrophoresed on a 0.8% agarose gel, eluted, and then, was finally used to prepare the cassette for inactivating the nrfA gene.

In order to prepare a threonine-producing strain having the inactivated nfrA gene, a threonin-producing strain (KCCM10910P), which was transformed with a pKD46 plasmid according to the method developed by Datsenko K A et al. (Proc Natl Acad Sci USA., (2000) 97:6640-6645), was prepared as a competent strain. Then, DNA of the cassette prepared for inactivating the nfrA gene was introduced to the strain to allow transformation.

The obtained strain was selected on a LB plate having chloramphenicol resistance. That is, a primer set of SEQ ID NOS: 5 and 6, which has a DNA sequence lying outside of two ends of an nfrA homologous sequence of the cassette for genomic inactivation, was used to thereby select colonies where the size of the resultant PCR product was reduced from 2.8 kb to 1.5 kb.

The primary recombinant strain having chloramphenicol resistance was removed from the pKD46 plasmid, and then, introduced with a pJW168 plasmid to remove the chloramphenicol marker gene from the microbial cells (Gene, (2000) 247, 255-264). Then, PCR using a primer set of SEQ ID NOS: 5 and 6 was performed to obtain 0.4 kb DNA product, indicating that the strain finally obtained had a reduced DNA size. Accordingly, the L-threonine-producing strain having the inactivated nfrA gene (KCCM10910PΔnfrA) was prepared.

1-2. Preparation of Threonine-Producing Strain Having Inactivated nfrB Gene

In order to prepare a threonine-producing strain having an inactivated nfrB gene (SEQ ID NO: 41), a cassette for inactivating an nfrB gene was prepared in the same manner as in the preparation of the cassette for inactivating the nfrA gene of Example 1-1. 1.1 kb DNA fragment was obtained by using a primer set of SEQ ID NOS: 8 and 9, and then, 1.2 kb DNA fragment was prepared by using a primer set of SEQ ID NOS: 7 and 10.

A method of preparing a threonin-producing strain having the inactivated nfrB gene was carried out by the same method described in Example 1-1, wherein a primer set of SEQ ID NOS: 11 and 12 was used to confirm the size of the resultant PCR product. Accordingly, the L-threonine-producing strain having the inactivated nfrB gene (KCCM10910PΔnfrB) was finally prepared.

1-3. Preparation of Threonine-Producing Strain Having Inactivated nfrAB Gene

In order to prepare a threonine-producing strain having an inactivated nfrAB gene (SEQ ID NO: 43), a cassette for inactivating an nfrAB gene was prepared in the same manner as in the preparation of the cassette for inactivating the nfrA gene of Example 1-1. 1.1 kb DNA fragment was obtained by using a primer set of SEQ ID NOS: 2 and 9, and then, 1.2 kb DNA fragment was prepared by using a primer set of SEQ ID NOS: SEQ ID NO: 1 and 10.

A method of preparing a threonin-producing strain having the inactivated nfrAB gene was carried out by the same method described in Example 1-1, wherein a primer set of SEQ ID NOS: 5 and 12 was used to confirm the size of the resultant PCR product. Accordingly, the L-threonine-producing strain having the inactivated nfrAB gene (KCCM10910PΔnfrAB) was finally prepared.

1-4. Preparation of Threonine-Producing Strain Having Inactivated Tsx Gene

In order to prepare a threonin-producing strain having an inactivated tsx gene (SEQ ID NO: 44), a cassette for inactivating a tsx gene was prepared in the same manner as in the preparation of the cassette for inactivating the nfrA gene of Example 1-1. 1.1 kb DNA fragment was obtained by using a primer set of SEQ ID NOS: 13 and 14, and then, 1.2 kb DNA fragment was prepared by using a primer set of SEQ ID NOS: 15 and 16.

A method of preparing the threonine-producing strain having the inactivated tsx gene was carried out by the same method described in Example 1-1, wherein a primer set of SEQ ID NOS: 17 and 18 was used to confirm the size of the resultant PCR product. Accordingly, the L-threonine-producing strain having inactivated tsx gene (KCCM10910PΔtsx) was finally prepared.

1-5. Preparation of Threonine-Producing Strain Having Inactivated fhuA Gene

In order to prepare a threonine-producing strain having an inactivated fhuA gene (SEQ ID NO: 46), a cassette for inactivating an fhuA gene was prepared according to the method of one-step inactivation described above. In order to obtain a DNA fragment with a base sequence having homology with a sequence of the fhuA gene, a primer set of SEQ ID NOS: 19 and 20 and a primer set of SEQ ID NOS: 21 and 22 were used, resulting in producing PCR products. In addition, in order to obtain a DNA fragment with a base sequence having chloramphenicol resistance, a primer set of SEQ ID NOS: 23 and 24 was used, resulting in producing a PCR product. Accordingly, these three resultant PCR products were electrophoresed on a 0.8% agarose gel, and then, eluted. PCR was performed by using these three eluted PCR products as templates and a primer set of SEQ ID NOS: 19 and 22 to prepare a cassette for inactivating the fhuA gene.

In order to prepare a threonine-producing strain having the inactivated fhuA gene, the cassette for inactivating the fhuA gene was prepared by the same method described in Example 1-1, wherein a primer set of SEQ ID NOS: 25 and 26 was used to confirm the size of the resultant PCR products. Accordingly, the L-threonine-producing strain having the inactivated fhuA gene (KCCM10910PΔfhuA) was finally prepared.

1-6. Preparation of Threonine-Producing Strain Having Inactivated lamB Gene

In order to prepare a threonine-producing strain having an inactivated lamB gene (SEQ ID NO: 48), a cassette for inactivating a lamB gene was prepared by the same method described in Example 1-1. 1.1 kb DNA fragment was obtained by using a primer set of SEQ ID NOS: 27 and 28, and then, 1.2 kb DNA fragment was prepared by using a primer set of SEQ ID NOS: 29 and 30.

A method of preparing the threonine-producing strain having the inactivated lamB gene was carried out by the same method described in Example 1-1, wherein a primer set of SEQ ID NOS: 31 and 32 was used to confirm the size of the resultant PCR product. Accordingly, the L-threonine-producing strain having inactivated lamB gene (KCCM10910PΔlamB) was finally prepared.

1-7. Preparation of Threonine-Producing Strain Having Inactivated btuB Gene

In order to prepare a threonine-producing strain having an inactivated btuB gene (SEQ ID NO: 50), a cassette for inactivating a btuB gene was prepared by the same method described in Example 1-1. 1.1 kb DNA fragment was obtained by using a primer set of SEQ ID NOS: 33 and 34, and then, 1.2 kb DNA fragment was prepared by using a primer set of SEQ ID NOS: 35 and 36.

A method of preparing the threonine-producing strain having the inactivated btuB gene was carried out by the same method described in Example 1-1, wherein a primer set of SEQ ID NOS: 37 and 38 was used to confirm the size of the resultant PCR product. Accordingly, the L-threonine-producing strain having the inactivated btuB gene (KCCM10910PΔbtuB) was finally prepared.

Example 2. Comparison in L-Threonine Productivity Among Recombinant Microorganisms The recombinant microorganisms prepared according to Example 1 were cultured in a threonine titer medium containing compositions shown in Table 1 below, in an Erlenmeyer flask. Then, it was confirmed whether the recombinant microorganisms had producibility of L-threonine.

TABLE 1

| Composition | Concentration (per liter) |
|---|---|
| Glucose | 70 g |
| $KH_2PO_4$ | 2 g |
| $(NH_4)_2SO_4$ | 27.5 g |
| $MgSO_4{\bullet}H_2O$ | 1 g |
| $FeSO_4{\bullet}H_2O$ | 5 mg |
| $MnSO_4{\bullet}H_2O$ | 5 mg |
| DL-methionine | 0.15 g |
| Yeast extract | 2 g |
| Calcium carbonate | 30 g |
| pH | 6.8 |

1 platinum loop of each of the 7 types of the *E. coli* strains of Example 1 and the KCCM10910P strain that were cultured overnight in the LB solid medium in an incubator at 33° C. was inoculated in 25 ml of a titer medium containing compositions shown in Table 1 above, and then, was cultured in an incubator at 33° C. and at 200 rpm for 48 hours.

TABLE 2

| Strain | Sugar consumption (g/L) 30 hr | L-threonine (g/L) 48 hr |
|---|---|---|
| KCCM 10910P (mother strain) | 22 | 34.5 |
| KCCM 10910PΔnfrA | 26 | 34.5 |
| KCCM 10910PΔnfrB | 26 | 34.4 |
| KCCM 10910PΔnfrAB | 26 | 34.4 |
| KCCM 10910PΔtsx | 25 | 34.4 |
| KCCM 10910PΔfhuA | 24 | 34.5 |
| KCCM 10910PΔlamB | 20 | 34.5 |
| KCCM 10910PΔbtuB | 21 | 34.5 |

As shown in Table 2 above, it was confirmed that the sugar consumption rates of the strains each having the inactivated nfrA, nfrB, nfrAB, tsx, and fhuA genes were higher than the sugar consumption rate of the mother strain (KCCM10910P). It was also confirmed that the production rate of the strains was not reduced during a 48 hour period. Meanwhile, it was confirmed that the sugar consumption rates of the strains each having the inactivated lamB and btuB genes were similar to the sugar consumption rate of the mother strain, or slightly slower than the sugar consumption rate of the mother strain. It was also confirmed that the concentrations of L-threonine shown in the strains of the culture after 48 hours were all similar. The strains each having the inactivated nfrA, nfrB, and nfrAB genes resulted in the same culturing results. That is, the case where one of the two genes was deleted and the case where both genes were deleted generated the same results.

Example 3. Preparation of Strains with Effective Mutation Combination and Comparison in L-Threonine Producibility Thereof 3-1. Preparation of Strains Having Simultaneously Inactivated nfrAB and fhuA Genes, Simultaneously Inactivated nfrAB and Tsx Genes, and Simultaneously Inactivated nfrAB, Tsx, and fhuA Genes In order to confirm whether the case where the combined inactivation of the nfrAB, fhuA, and tsx genes having increased sugar consumption capacity has further sugar consumption capacity in the L-threonine-producing strains, a KCCM10910PΔnfrABΔ fhuA strain, a KCCM10910PΔnfrABΔtsx strain, and a KCCM10910PΔnfrABΔtsxΔ fhuA strain were prepared. In order to prepare these strains, strains each having the inactivated fhuA and tsx genes were prepared in accordance with the KCCM10910PΔ nfrAB strain of Example 1-3 in the same manner as described in Example 1 (resulting in KCCM10910PΔnfrABΔfhuA and KCCM10910PΔnfrABΔtsx strains). In addition, a strain having the inactivated fhuA gene was prepared in accordance with the KCCM10910PΔnfrABΔtsx strain, thereby finally preparing a KCCM10910PΔnfrABΔ tsxΔfhuA strain.

As shown in Table 2, the strains having the inactivated nfrA, nfrB, and nfrAB genes were determined to have the same effects as one another. In this regard, in the preparation of strains with effective mutation combinations, the strains having the inactivated tsx and fhuA genes were prepared by using the strain having the inactivated nfrAB gene. However, the effects of the strains having the inactivated tsx and fhuA genes were determined to be the same as the effects of the strain having the inactivated nfrA gene only, the inactivated nfrB gene only, or the simultaneously inactivated nfrA and nfrB genes.

3-2. Comparison in L-Threonine Producibility of Strains with Effective Mutation Combinations In order to compare the L-threonine producibility of the strains with effective mutation combinations prepared above, a medium containing compositions shown in Table 1 above was used to culture strains in the same manner as described above. The results are shown in Table 3 below.

TABLE 3

| Strain | Sugar consumption (g/L) 30 hr | L-threonine (g/L) 48 hr |
|---|---|---|
| KCCM10910P (mother strain) | 22 | 34.5 |
| KCCM10910PΔnfrAB | 26 | 34.4 |
| KCCM10910PΔnfrABΔfhuA | 28 | 34.5 |
| KCCM10910PΔnfrABΔtsx | 28 | 34.4 |
| KCCM10910PΔnfrABΔtsxΔfhuA | 29 | 34.5 |

As a result of a potency test on the KCCM10910PΔnfrABΔfhuA strain, the KCCM10910PΔnfrABΔtsx strain, and the KCCM10910PΔnfrABΔtsxΔfhuA strain, each prepared in accordance with the combined inactivation of the nfrAB, fhuA, and tsx genes having increased sugar consumption capacity, it was confirmed that the strain in which the fhuA gene or the tsx gene was further inactivated in addition to the mutation by the nfrAB gene only increased the sugar consumption capacity. Accordingly, the transformed KCCM10910PΔnfrAB strain showing increased sugar consumption capacity was named '*E. coli* CA03-8253P', and then, was deposited at the Korean Culture Center of Microorganisms (KCCM) on Dec. 13, 2013 (Accession No: KCCM11501P).

Example 4. Preparation of Strain Having Inactivated Phage Receptor by Using KCCM-10132 and Comparison in Threonine Producibility Thereof 4-1. Preparation of Strain Having Inactivated Phage Receptor by Using KCCM10132

The 10 types of strains each having an inactivated phage receptor were prepared by using a KCCM-10132 strain (see Table 4 below) in the same manner as described in Examples 1 and 3, in accordance with the 7 types of the inactivation cassettes of Example 1. The KCCM-10132 strain was disclosed in Korean Patent No: 10-0270510 as a strain having threonine producibility derived from *E. coli.*

4-2. Preparation of Strain Having Inactivated Phage Receptor by Using KCCM10132 and Comparison in Threonine Producibility Thereof The 10 types of the strains each having the inactivated phage receptor that were prepared by using the KCCM-10132 strain of Example 4-1 and the mother strain (KCCM-10132) were cultured in a medium containing the compositions shown in Table 1 by the same method as described in Example 2. Then, the cultured strains were evaluated by comparing the producibility of threonine thereof.

TABLE 4

| Strain | Sugar consumption (g/L) 30 hr | L-threonine (g/L) 48 hr |
|---|---|---|
| KCCM-10132 (mother strain) | 32 | 20.2 |
| KCCM-10132ΔnfrA | 35 | 20.2 |
| KCCM-10132ΔnfrB | 35 | 20.1 |
| KCCM-10132ΔnfrAB | 36 | 20.2 |
| KCCM-10132Δtsx | 35 | 20.2 |
| KCCM-10132ΔfhuA | 36 | 20.1 |
| KCCM-10132ΔlamB | 31 | 20.2 |
| KCCM-10132ΔbtuB | 30 | 20.1 |
| KCCM-10132ΔnfrABΔfhuA | 38 | 20.2 |
| KCCM-10132ΔnfrABΔtsx | 38 | 20.1 |
| KCCM-10132ΔnfrABΔtsxΔfhuA | 39 | 20.2 |

As shown in Table 4 above, it was confirmed that the sugar consumption rates of the strains each having the inactivated nfrA, nfrB, nfrAB, tsx, and fhuA genes were higher than the sugar consumption rate of the mother strain (KCCM-10132). It was also confirmed that the production rate of the strains was not reduced in a 48 hour period. Meanwhile, it was confirmed that the sugar consumption rates of the strains each having the inactivated lamB and the btuB genes were similar to the sugar consumption rate of the mother strain, or slightly slower than the sugar consumption rate of the mother strain. It was also confirmed that the concentrations of L-threonine shown in the strains of the culture after 48 hours were all similar. It was also confirmed that the strains each having the simultaneously inactivated nfrAB, fhuA, nfrAB and tsx genes and the simultaneously inactivated nfrAB, tsx, and fhuA genes had improved sugar consumption rates in comparison to the sugar consumption rate of the strain having the inactivated nfrAB gene only.

Example 5. Preparation of Strain Having Inactivated Phage Receptor by Using KCCM11166P and Comparison in Threonine Producibility Thereof 5-1. Preparation of Strain Having Inactivated Phage Receptor by Using KCCM11166P 7 types of tryptophan-producing strains each having an inactivated phage receptor were prepared by using a KCCM11166P (Korean Patent NO: 10-1261147) in the same manner as described in Example 1, in accordance with the 7 types of the inactivation cassettes of Example 1.

5-2. Preparation of Strain Having Inactivated Phage Receptor by Using KCCM11166P and Comparison in Threonine Producibility Thereof In order to evaluate the producibility of the 7 types of the tryptophan-producing strains each having the inactivated phage receptor prepared by using the KCCM11166P strain of Example 5-1, a medium containing compositions shown in Table 5 below was used. That is, the microbial cells were inoculated by a platinum loop, and then, were cultured overnight in the LB solid medium. Afterwards, 1 platinum loop of each of the microbial cells was inoculated in 25 ml of titer medium containing the compositions shown in Table 5 below, and then, was cultured in an incubator at 37° C. and at 200 rpm for 48 hours. The results obtained therefrom are shown in Table 6 below.

TABLE 5

| Composition | Concentration (per liter) |
|---|---|
| Glucose | 60 g |
| $K_2HPO_4$ | 1 g |
| $(NH_4)_2SO_4$ | 10 g |
| $MgSO_4 \cdot H_2O$ | 1 g |
| NaCl | 1 g |
| Sodium citrate | 5 g |
| Yeast extract | 2 g |
| Calcium carbonate | 40 g |
| Phenylalanine | 0.15 g |
| Thyrosine | 0.1 g |
| pH | 6.8 |

TABLE 6

| Strain | Sugar consumption (g/L) 33 hr | OD | L-tryptophan (g/L) 48 hr |
|---|---|---|---|
| KCCM11166P | 56.8 | 14.0 | 7.2 |
| KCCM11166PΔnfrA | 59.5 | 13.5 | 7.2 |
| KCCM11166PΔnfrB | 59.5 | 13.5 | 7.2 |
| KCCM11166PΔnfrAB | 59.5 | 13.5 | 7.2 |
| KCCM11166PΔtsx | 60.2 | 14.3 | 7.1 |
| KCCM11166PΔfhuA | 59.5 | 13.7 | 7.1 |
| KCCM11166PΔlamB | 57.0 | 14.0 | 7.2 |
| KCCM11166PΔbtuB | 56.2 | 13.0 | 7.1 |

As shown in Table 6 above, in the case of the deletion of each of the nfrA, nfrB, nfrAB, tsx, and fhuA genes, it was confirmed that the amounts of tryptophan produced in the strains each having the inactivated nfrA, nfrB, nfrAB, tsx, and fhuA genes were similar while the sugar consumptions rate of the strains each having the inactivated nfrA, nfrB, nfrAB, tsx, and fhuA genes were slightly higher than others. Meanwhile, in the case of the deletion of each of the lamB and btuB genes, it was confirmed that the amounts of tryptophan produced by the strains each having the inactivated lamB and btuB genes or the sugar consumption rates of the strains each having the inactivation of lamB and btuB genes were not changed.

Example 6. Preparation of Strains with Effective Mutation Combination and Comparison in L-Tryptophan Producibility Thereof 6-1. Preparation of L-Tryptophan-Producing Strains Having Simultaneously Inactivated nfrAB and fhuA Genes, Simultaneously Inactivated nfrAB and Tsx Genes, and Simultaneously Inactivated nfrAB, tsx, and fhuA Genes In order to confirm whether the case where the combined inactivation of the nfrAB, fhuA, and tsx genes having increased sugar consumption capacity has further sugar consumption capacity in the tryptophan-producing strains, a KCCM11166PΔnfrABΔ fhuA strain, a KCCM11166PΔnfrABΔtsx strain, and a KCCM11166PΔnfrABΔtsxΔ fhuA strain were prepared.

6-2. Comparison in L-Tryptophan Producibility of Strains with Effective Mutation Combination In order to compare the L-tryptophan producibility of the three types of the strains prepared according to Example 6-1, a medium containing compositions shown in Table 5 above was used to culture the strains in the same manner as described in Example 5. The results are shown in Table 7 below.

TABLE 7

| Strain | Sugar consumption (g/L) 33 hr | OD | L-tryptophan (g/L) 48 hr |
|---|---|---|---|
| KCCM11166P | 56.8 | 14.0 | 7.2 |
| KCCM11166PΔnfrAB | 59.5 | 13.5 | 7.2 |
| KCCM11166PΔnfrABΔtsx | 61.0 | 14.0 | 7.2 |
| KCCM11166PΔnfrABΔfhuA | 60.5 | 13.8 | 7.1 |
| KCCM11166PΔnfrABΔtsxΔfhuA | 62.0 | 14.0 | 7.2 |

As a result of a potency test on the tryptophan-producing strains with effective mutation combinations, it was confirmed that the strains in which the fhuA gene or/and the tsx gene was further inactivated in addition to the mutation by the nfrAB gene only increased the sugar consumption capacity.

It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments of the present invention have been described with reference to the figures, it will be understood by those of ordinary skill in the art that various changes in form and details may be made therein without departing from the spirit and scope of the present invention as defined by the following claims.

[Accession Number]

Depositary institution: Korean Culture Center of Microorganisms (international)

Accession number: KCCM11501P

Depositary date: Dec. 13, 2013

The invention claimed is:

1. A recombinant microorganism of the genus *Escherichia* producing L-amino acid in which at least one of NfrA and NfrB is inactivated and tsx is inactivated, wherein the recombinant microorganism has a producibility of the L-amino acid.

2. The recombinant microorganism of claim 1, wherein the NfrA comprises the amino acid sequence of SEQ ID NO: 40, the NfrB comprises the amino acid sequence of SEQ ID NO: 42, and the Tsx comprises the amino acid sequence of SEQ ID NO: 45.

3. The recombinant microorganism of claim 1, wherein FhuA is further inactivated.

4. The recombinant microorganism of claim 3, the FhuA comprises the amino acid sequence of SEQ ID NO: 47.

5. The recombinant microorganism of claim 1, wherein the L-amino acid is L-threonine or L-tryptophan.

6. The recombinant microorganism of claim 1, wherein the recombinant microorganism is *Escherichia coli.*

7. A method of producing an L-amino acid, the method comprising:

culturing the recombinant microorganism of claim 1; and collecting an L-amino acid from the culture.

8. The method of claim 7, wherein the L-amino acid is L-threonine or L-tryptophan.

9. The method of claim 7, wherein the NfrA comprises an amino acid sequence of SEQ ID NO: 40, the NfrB comprises the amino acid sequence of SEQ ID NO: 42, and the Tsx comprises the amino acid sequence of SEQ ID NO: 45.

10. The method of claim 7, wherein FhuA is further inactivated.

11. The method of claim 10, wherein the FhuA comprises the amino acid sequence of SEQ ID NO: 47.

12. The method of claim 7, wherein the recombinant microorganism is *Escherichia coli.*

13. The recombinant microorganism of claim 1, wherein the recombinant microorganism has an increased sugar consumption rate compared to a microorganism of the genus *Escherichia* producing L-amino acid in which NfrA and NfrB are not inactivated.

* * * * *